US012755848B2

(12) United States Patent
Kumar et al.

(10) Patent No.: US 12,755,848 B2
(45) Date of Patent: Oct. 6, 2026

(54) MACHINE LEARNING FOR EFFECTIVE PATIENT PLANNING

(71) Applicant: MatrixCare, Inc., Bloomington, MN (US)

(72) Inventors: Vivek Kumar, Eden Prairie, MN (US); Coleen Danielson, Fergus Falls, MN (US)

(73) Assignee: MatrixCare, Inc., Bloomington, MN (US)

( * ) Notice: Subject to any disclaimer, the term of this patent is extended or adjusted under 35 U.S.C. 154(b) by 295 days.

(21) Appl. No.: 18/165,822

(22) Filed: Feb. 7, 2023

(65) Prior Publication Data

US 2023/0307140 A1 Sep. 28, 2023

Related U.S. Application Data

(60) Provisional application No. 63/324,478, filed on Mar. 28, 2022.

(51) Int. Cl.
*G16H 50/30* (2018.01)
*G06N 20/00* (2019.01)

(52) U.S. Cl.
CPC ............. *G16H 50/30* (2018.01); *G06N 20/00* (2019.01)

(58) Field of Classification Search
None
See application file for complete search history.

(56) References Cited

U.S. PATENT DOCUMENTS

2012/0041772 A1 * 2/2012 Ebadollahi ............. G16H 50/70 705/2
2022/0367031 A1 * 11/2022 Ahmad .................. G16H 50/30
2022/0392642 A1 * 12/2022 Dasi ........................ G16H 50/50
2023/0170093 A1 * 6/2023 Hussain ................... G06N 3/08 705/2
2023/0178237 A1 * 6/2023 Griffin .................. G16H 20/10 705/2

FOREIGN PATENT DOCUMENTS

WO WO-2020081609 A1 * 4/2020 ........... A61B 5/0075

OTHER PUBLICATIONS

Yassine, A. (2021). PDT-Space: Automatic interstitial photodynamic therapy planning and optimization (Order No. 28413692). Available from ProQuest Dissertations and Theses Professional. (2557220664). (Year: 2021).*

* cited by examiner

*Primary Examiner* — Emily Huynh
(74) *Attorney, Agent, or Firm* — Patterson + Sheridan, LLP

(57) ABSTRACT

Techniques for improved machine learning are provided. Resident data describing a first condition of a first resident of a residential care facility is received. An optimized treatment plan is selected for the first resident by extracting a first plurality of resident attributes, from the resident data, generating a first approach to remediate the first condition, and generating a first predicted recovery score by inputting the first approach and the first plurality of resident attributes into a trained machine learning model. The optimized treatment plan is implemented for the first resident.

20 Claims, 15 Drawing Sheets

MACHINE LEARNING FOR EFFECTIVE PATIENT PLANNING

CROSS-REFERENCE TO RELATED APPLICATIONS

This application claims priority to U.S. Provisional Patent Application No. 63/324,478, filed Mar. 28, 2022, the entire content of which is incorporated herein by reference in its entirety.

INTRODUCTION

Embodiments of the present disclosure relate to machine learning. More specifically, embodiments of the present disclosure relate to using machine learning to generate and evaluate treatment plans.

In conventional healthcare settings, such as in residential care facilities (e.g., nursing homes), a wide variety of user, patient, or resident characteristics are assessed and monitored in an effort to reduce or prevent worsening any resident's condition. Additionally, whenever patient or resident problems arise (e.g., wounds, illnesses, and the like), care plans must be devised to attempt to ameliorate the issue(s). However, these conditions and issues are tremendously complex, and have a myriad of causes as well as a vast variety of potential solutions. Without appropriate care planning, these problems can lead to clinically significant negative outcomes and complications.

Conventionally, healthcare providers (e.g., doctors, nurses, caregivers, and the like) strive to provide adequate care planning using manual assessments (e.g., relying on subjective experience). However, such conventional approaches are entirely subjective (relying on the expertise of individual caregiver to recognize and care for possible concerns), and frequently fail to identify the most optimal care plans for a variety of users. Further, given the vast complexity involved in these plans, it is simply impossible for healthcare providers to evaluate all relevant data and alternatives in order to select optimal plans.

Improved systems and techniques to automatically generate evaluate and such plans are needed.

SUMMARY

According to one embodiment presented in this disclosure, a method is provided. The method includes: receiving treatment data describing a treatment plan for a resident of a residential care facility; generating a first recovery score based on the treatment data, wherein the first recovery score indicates success of the treatment plan in treating the resident; training a machine learning model to predict resident recovery based on the first recovery score; and deploying the trained machine learning model.

According to one embodiment presented in this disclosure, a method is provided. The method includes: receiving resident data describing a first condition of a first resident of a residential care facility; selecting an optimized treatment plan for the first resident, comprising: extracting a first plurality of resident attributes, from the resident data, for the first resident; generating a first approach to remediate the first condition; and generating a first predicted recovery score by inputting the first approach and the first plurality of resident attributes into a trained machine learning model; and implementing the optimized treatment plan for the first resident.

The following description and the related drawings set forth in detail certain illustrative features of one or more embodiments.

DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
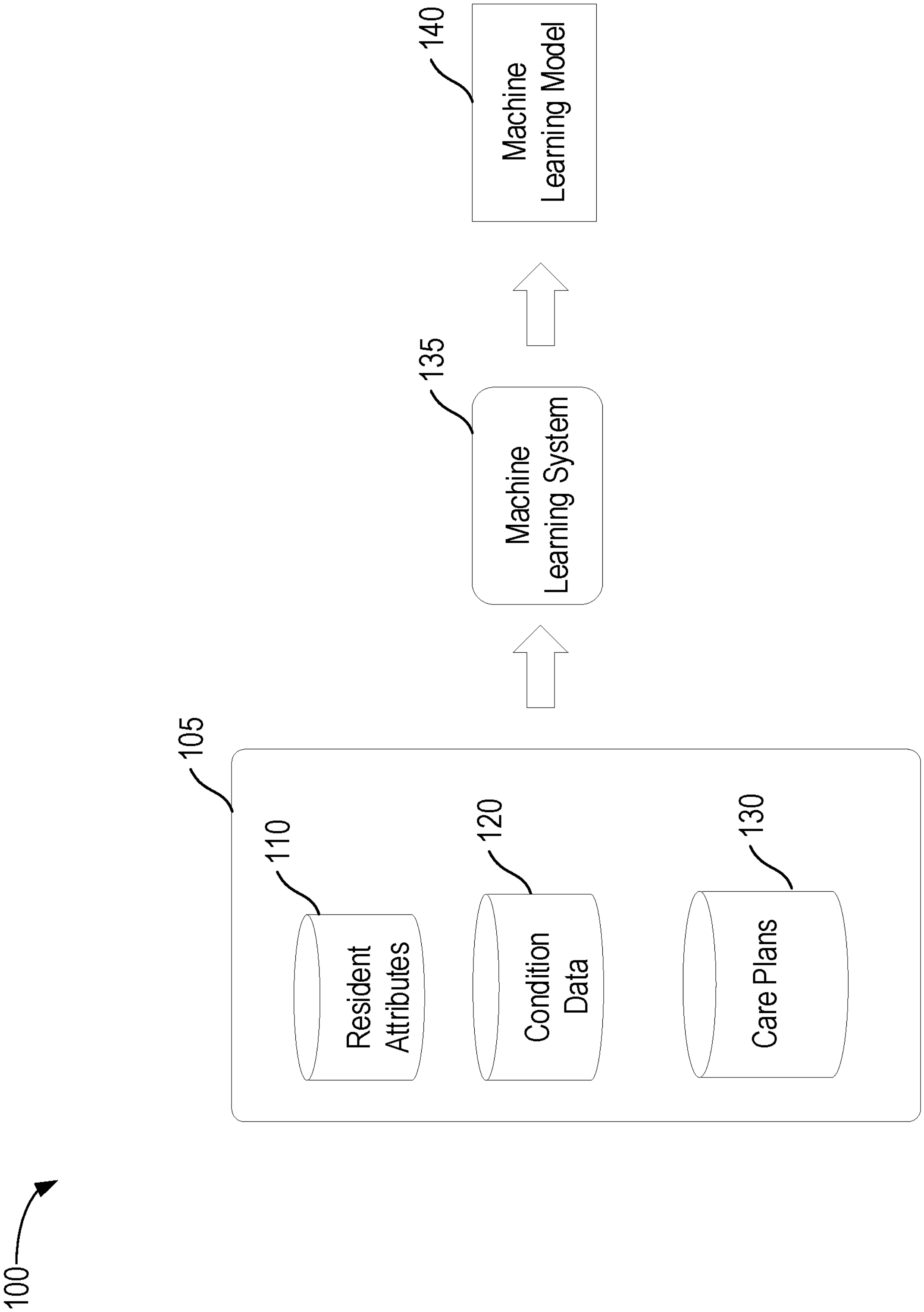
FIG. 1 depicts an example workflow for training machine learning models based on historical data.

Aspects of the present disclosure provide apparatuses, methods, processing systems, and computer-readable mediums for improved machine learning to generate and evaluate treatment and care plans.

In some embodiments, a machine learning model (also referred to in some aspects as a care model or a treatment model) can be trained and used as a tool for clinicians (e.g., nurses, caregivers, doctors, and the like) to assist in generating and evaluating care plans for users (e.g., patients, residents of a long-term care facility, and the like), thereby improving care, and preventing potentially significant negative outcomes. In some embodiments, by monitoring for changes in the conditions for each user, the system is able to identify those in need of revised care plans, and can assist with reallocating resources and driving targeted interventions to help mitigate, prevent, or reduce the effect of a myriad of problems and disorders.

In conventional settings, caretakers must rely on subjective assessments and plans (e.g., manually determining proper treatment plans) to care for residents. In addition to this inherently subjective and inaccurate approach, many conventional systems are largely static and have difficultly responding to dynamic situations (e.g., changing resident conditions) which are common in residential facilities. Moreover, the vast number and variety of alternative treatments that can be used, as well as the significant amounts of data available for each resident, render accurate analysis and selection of proper treatments impossible to adequately perform manually or mentally. Aspects of the present disclosure can not only reduce or prevent this subjective review, but can further prevent wasted time and computational expense spent reviewing vast amounts of irrelevant data and sub-optimal plans. Further, aspects of the present disclosure enable more accurate evaluations, more efficient use of computational resources, and overall improved outcomes for residents.

Embodiments of the present disclosure can generally enable proactive and quality care for users, as well as dynamic and targeted interventions, that help to prevent or reduce adverse events due to a variety of issues and conditions. This autonomous and continuous updating based on changing conditions with respect to individual users enables a wide variety of improved results, including not only improved outcomes for the users (e.g., reduced negative outcomes, early identification of optimal plans, targeted interventions, and the like) but also improved computational efficiency and accuracy of the evaluation and solution process.

In some embodiments, a variety of historical resident data can be collected and evaluated to train one or more machine learning models. During such training, the machine learning model(s) can learn a set of features (e.g., resident attributes) and/or a set of weights for such features. These features and weights can then be used to automatically and efficiently process new user data in order to generate and evaluate improved care plans. In some aspects, the model may be trained during a training phase, and then be deployed as a static model that, once deployed, remains fixed. In other embodiments, the model may be refined or updated (either periodically or upon specified criteria). That is, during use in evaluating and generating in potential plans, the model may be refined based on feedback from users, caregivers, and the like. For example, if a clinician indicates that a care plan was successful in remediating a resident's condition (regardless of whether the model suggested the plan), the model may be refined based on this indication. Similarly, if a clinician indicates that a care plan failed to help the condition, the model may be refined to reflect this new data.

Example Workflow for Training Machine Learning Models Using Historical Data

FIG. 1 depicts an example workflow 100 for training machine learning models based on historical data.

In the illustrated workflow 100, a set of historical data 105 is evaluated by a machine learning system 135 to generate one or more machine learning models 140. In embodiments, the machine learning system 135 may be implemented using hardware, software, or a combination of hardware and software. The historical data 105 generally includes data or information associated with one or more residents (also referred to as users or patients) from one or more prior points in time. That is, the historical data 105 may include, for one or more residents, a set of one or more snapshots of the resident's characteristics or attributes at one or more points in time. For example, the historical data 105 may include attributes for a set of residents residing in one or more long-term care facilities. In some embodiments, the historical data 105 includes indications of when any of the resident attributes changed (e.g., records indicating the updated attributes whenever a change occurs). The historical data 105 may generally be stored in any suitable location. For example, the historical data 105 may be stored within the machine learning system 135, or may be stored in one or more remote repositories, such as in a cloud storage system.

In the illustrated example, the historical data 105 includes, for each resident reflected in the data, a set of one or more resident attributes 110, condition data 120, and care plans 130. In some embodiments, as discussed above, the historical data 105 includes data at multiple points in time for each resident. That is, for a given resident, the historical data 105 may include multiple sets of resident attributes 110 (one set for each relevant point in time), and the like. In some embodiments, the data contained within the resident attributes 110, condition data 120, and care plans 130 are associated with timestamps or other indications of the relevant time or period for the data. In this way, the machine learning system 135 can identify the relevant data for any given point or window of time. For example, for a given care plan 130 at a given time, the machine learning system 135 can identify all the relevant data surrounding this time (e.g., the resident attributes 110 and/or condition data 120 at the time the plan was instantiated, within a predefined window before the time, such as one month prior, and the like).

In some embodiments, the historical data 105 may be collectively stored in a single data structure. For example, the resident attributes 110, condition data 120, and/or care plans 130 may each be represented in a resident profile (with indications of any changes over time), or as a sequence of structures (e.g., a set of profiles or forms, each corresponding to a particular point or window in time and containing attributes for that time). In some portions of the present discussion, the various components of the historical data 105 are described with reference to a single resident for conceptual clarity (e.g., resident attributes 110 of a single resident). However, it is to be understood that the historical data 105 can generally include such data for any number of residents.

As discussed in more detail below, the resident attributes 110 generally correspond to a set of one or more specified features, attributes, or characteristics describing the resident(s). For example, the resident attributes 110 may include characteristics such as resident age, diagnoses or disorders they have, assistance they require (e.g., whether they need assistance walking), and the like. In at least one embodiment, the resident attributes 110 can include information or data generated by machine learning models. For example, the resident attributes 110 may include a fall risk score indicating a probability that the resident will fall and/or a predicted severity of such a fall (generated by one or more trained models based on various resident data), an acuity score indicating the acuity or degree of care needed by the resident (generated by one or more trained models based on various resident data), a depression risk score indicating a probability that the resident has or will develop depression (generated by one or more trained models based on various resident data), and the like.

In some embodiments, the historical data 105 can indicate, for each specified feature, whether the corresponding resident has the attribute (or the value of the attribute) (at the relevant time). In some embodiments, the resident attributes 110 are curated or selected based on their impact on how residents respond to care plans. For example, in one aspect, a user (e.g., a clinician) may manually specify attributes that have a high impact on care plan success. In some embodiments, some or all of the attributes may be inferred or learned (e.g., using one or more feature selection techniques). For example, one or more machine learning models or feature selection algorithms may be used to identify specific attributes (or to determine dynamic weights for each attribute) based on their impact on the success of care plans.

As discussed in more detail below, the condition data 120 generally corresponds to information relating to a set of specified assessments, problems, conditions, disorders, or issues relating to the functional state of the resident. For example, the condition data 120 may indicate problems experienced by or reported by the user or a clinician, such as whether the resident experiences pain, whether the resident is ill, and the like. The condition data 120 can generally indicate, for each condition, whether the corresponding resident has the specified condition. In some embodiments, the condition data 120 can further indicate details about each condition, such as the severity, time of onset, and the like. In some embodiments, the condition data 120 includes data for each problem or issue that the machine learning system 135 is configured to evaluate. That is, for each possible condition for which a care plan can or should be generated, the condition data 120 may include data for the condition.

As discussed in more detail below, the care plans 130 can generally indicate a set of details for how clinicians, caregivers, nurses, doctors, or other users treat or otherwise respond to each condition of the resident. In one such aspect, for each problem reflected in the condition data 120, the care plans 130 may indicate one or more goals such as partial or total amelioration of the problem, as well as one or more approaches to achieve that goal. For example, if a specific problem includes the user experiencing leg pain, the goals may include partial amelioration by some future time (e.g., 50% reduction in pain within 2 weeks) and total remediation by a second future time (e.g., within 2 months). The approach(es) to achieve such goal(s) may include specific interventions, treatments, therapies, assessments, and the like. For example, the approaches may include daily assessment of the pain level, physical therapy, pain medications, and the like.

In an embodiment, the care plans 130 are crafted by clinicians (e.g., nurses or doctors) for the resident. That is, the care plans 130 represent historical plans that were defined by users to treat or mitigate prior conditions for one or more residents. As discussed below in more detail, the machine learning system 135 can generally evaluate these historical care plans 130 to determine how effective they were (e.g., whether they remediated the resident's issue, how quickly the issue resolved, and the like). One or more machine learning models 140 can then be trained to generate and/or score new care plans to indicate whether they should be used (e.g., how likely they are to remediate an issue, how long it will likely take, and the like) based on various resident attributes.

Although the illustrated historical data 105 includes several specific components including resident attributes 110, condition data 120, and care plans 130, in some embodiments, the historical data 105 used by the machine learning system 135 may include fewer components (e.g., a subset of the illustrated examples) or additional components not depicted. Additionally, though the illustrated example provides general groupings of data to aid understanding, in some embodiments, the historical data 105 may be represented using any number of groups. For example, the condition data 120 may be reflected in the resident attributes 110.

As illustrated, the machine learning system 135 generates one or more machine learning models 140 based on the historical data 105. The machine learning model 140 generally specifies a set of weights for the various features or attributes of the historical data 105. In some embodiments, the machine learning model 140 specifies weights specifically for each individual feature (e.g., for each attribute in the set of attributes 110). For example, a first attribute may be associated with a lower weight than a second attribute. Similarly, in some embodiments, the machine learning model 140 specifies different weights depending on the severity of the feature (e.g., depending on the severity of a disorder or diagnosis). In some embodiments, the machine learning model 140 specifies weights for groups of features (e.g., a first weight for diagnoses-related resident attributes, a second weight for medication-related attributes, and so on).

In at least one embodiment, the machine learning model 140 can specify weights for one or more individual features, as well as weights for one or more broader categories. For example, the various diagnosis-related attributes may be individually weighted to generate an overall score or value for the diagnosis portion of the resident attributes 110 (e.g., a weighted sum or average). This value can then be weighted (along with the other groups of input data) to generate an overall value for the resident, considering all attributes (e.g., using a weighted sum or average).

In some embodiments, the specific features considered by the machine learning model 140 (e.g., the specific resident attributes 110) are manually defined and curated. For example, the specific features may be defined by a subject-matter expert. In other embodiments, the specific features are learned during a training phase.

For example, the machine learning system 135 may process the historical data 105 for a given resident at a given time as input to the machine learning model 140, and compare the generated likelihood of recovery using the historical care plan 130 to a ground-truth (e.g., a recovery score indicating whether the resident actually recovered). The difference between the generated and actual recovery scores can be used to refine the weights of the machine learning model 140, and the model can be iteratively refined (e.g., using data from multiple residents and/or multiple points in time) to accurately evaluate care plans.

In some embodiments, during or after training, the machine learning system 135 may prune the machine learning model 140 based in part on the learned weights. For example, if the learned weight for a given feature (e.g., a specific resident attribute 110) is below some threshold (e.g., within a threshold distance from zero), the machine learning system 135 may determine that the feature has no impact (or negligible impact) on the efficacy of care plans. Based on this determination, the machine learning system 135 may cull or remove this feature from the machine learning model 140 (e.g., by removing one or more neurons, in the case of a neural network). For future evaluations, the machine learning system 135 need not receive data relating to these removed features (and may refrain from processing or evaluating the data if it is received). In this way, the machine learning model 140 can be used more efficiently (e.g., with reduced computational expense and latency) to yield accurate evaluations.

In some embodiments, the machine learning system 135 can generate multiple machine learning models 140. For example, a separate machine learning model 140 may be generated for each facility (e.g., with a unique model for each specific long-term residential care facility), or for each region (e.g., with a unique model for each country). This may allow the machine learning system 135 to account for facility-specific, region-specific, or culture-specific changes (e.g., due to climate, average sunlight, and the like). In other embodiments, the machine learning system 135 generates a universal machine learning model 140. In at least one embodiment, the machine learning model 140 may use similar considerations (e.g., location, region, and the like) as an input feature.

In some embodiments, the machine learning system 135 outputs the machine learning model 140 to one or more other systems for use. That is, the machine learning system 135 may distribute the machine learning model 140 to one or more downstream systems, each responsible for one or more facilities. For example, the machine learning system 135 may deploy the machine learning model 140 to one or more servers associated with specific care facilities, and these servers may use the model to evaluate care plans for residents at the specific facility. In at least one embodiment, the machine learning system 135 can itself use the machine learning model to evaluate care plans across one or more locations.

Example Workflow for Generating Training Data for Machine Learning

Figure 2:
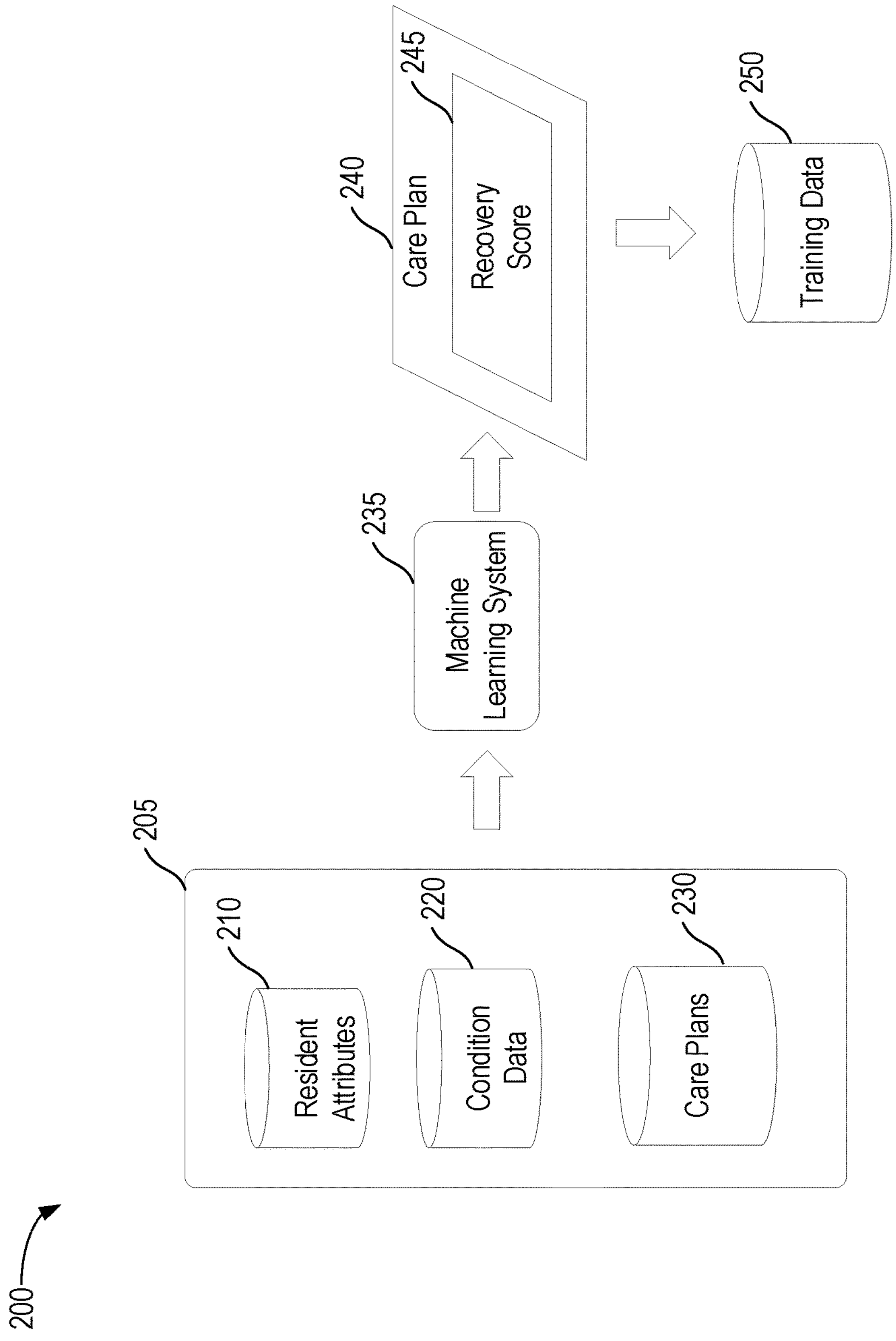
FIG. 2 depicts an example workflow for generating training data to drive improved care planning.

FIG. 2 depicts an example workflow 200 for generating training data to drive improved care planning.

In the illustrated workflow 200, a set of historical data 205 is evaluated by a machine learning system 235 to generate recovery scores 245 for prior care plans 240, which are used to form training data 250. This training data 250 can then be used to train one or more machine learning models, such as machine learning model 140 of FIG. 1.

In embodiments, the machine learning system 235 may be implemented using hardware, software, or a combination of hardware and software. In some embodiments, the machine learning system 235 corresponds to the machine learning system 135 of FIG. 1. That is, the same machine learning system may both generate training data 250, and use it to train models. In other embodiments, one or more systems may generate the training data 250, while one or more other systems use the training data 250 to train models.

The historical data 205 generally includes data or information associated with one or more residents (also referred to as users or patients) from one or more prior points in time, as discussed above. For example, the historical data 205 may include attributes for a set of residents residing in one or more long-term care facilities. The historical data 205 may generally be stored in any suitable location. For example, the historical data 205 may be stored within the machine learning system 235, or may be stored in one or more remote repositories, such as in a cloud storage system.

In the illustrated example, as discussed above, the historical data 205 includes, for each resident reflected in the data, a set of one or more resident attributes 210, condition data 220, and care plans 230. In some embodiments, as discussed above, the historical data 205 includes data at multiple points in time for each resident. That is, for a given resident, the historical data 205 may include multiple sets of resident attributes 210 (one set for each relevant point in time), and the like. In some embodiments, the data contained within the resident attributes 210, condition data 220, and care plans 230 are associated with timestamps or other indications of the relevant time or period for the data. In this way, the machine learning system 235 can identify the relevant data for any given point or window of time. For example, for a given care plan 230 at a given time, the machine learning system 235 can identify all the relevant data surrounding this time (e.g., the resident attributes 210 and/or condition data 220 at the time the plan was instantiated, within a predefined window before the time, such as one month prior, and the like).

In some embodiments, the historical data 205 may be collectively stored in a single data structure. For example, the resident attributes 210, condition data 220, and/or care plans 230 may each be represented in a resident profile (with indications of any changes over time), or as a sequence of structures (e.g., a set of profiles or forms, each corresponding to a particular point or window in time and containing attributes for that time). In some portions of the present discussion, the various components of the historical data 205 are described with reference to a single resident for conceptual clarity (e.g., resident attributes 210 of a single resident). However, it is to be understood that the historical data 205 can generally include such data for any number of residents.

As discussed above, the resident attributes 210 generally correspond to a set of one or more specified features, attributes, or characteristics describing the resident(s) (such as fall risk, depression risk, acuity score, demographic data, and the like), the condition data 220 generally corresponds to information relating to a set of specified assessments, problems, conditions, disorders, or issues relating to the functional state of the resident, and the care plans 230 can generally indicate a set of details for how clinicians, caregivers, nurses, doctors, or other users treat or otherwise respond to each condition of the resident. For example, for each problem reflected in the condition data 220, the care plans 230 may indicate one or more goals such as partial or total amelioration of the problem, as well as one or more approaches to achieve that goal.

As discussed above, the care plans 230 may have been crafted by clinicians (e.g., nurses or doctors) for the resident. That is, the care plans 230 represent historical plans that were defined by users to treat or mitigate prior conditions for one or more residents.

Although the illustrated historical data 205 includes several specific components including resident attributes 210, condition data 220, and care plans 230, in some embodiments, the historical data 205 used by the machine learning system 235 may include fewer components (e.g., a subset of the illustrated examples) or additional components not depicted. Additionally, though the illustrated example provides general groupings of data to aid understanding, in some embodiments, the historical data 205 may be represented using any number of groups. For example, the condition data 220 may be reflected in the resident attributes 210.

In the illustrated workflow 200, the machine learning system 235 can generally evaluate these historical care plans 230 to determine how effective they were (e.g., whether they remediated the resident's issue, how quickly the issue resolved, and the like) in order to generate, for each respective care plan, a corresponding recovery score 245. In some embodiments, the recovery score 245 is one or more numerical values indicating the efficacy of a given care plan 240.

For example, the recovery score 245 may indicate a probability that the care plan 240 will ameliorate or remediate the corresponding condition(s), a length of time that is expected to pass until the condition(s) are mitigated, and the like.

As illustrated, the recovery score 245 is used to create a training exemplar 240 including the corresponding care plan. In an embodiment, the exemplar 240 also includes the relevant resident attributes 210 (which may include other conditions of the resident). That is, the exemplar 240 can indicate the resident attributes 210 at a given time or window of time (e.g., just before the care plan 230 was generated, during use of the care plan, and the like). This data can be used as input to train the model, while the determined recovery score 245 is used as target output. In some embodiments, the exemplar 240 also includes the specifics of the care plan. That is, the model may be trained to receive, as input, one or more goal(s) specified in the care plan and/or one or more approach(es) specified in the care plan. This can allow the model to predict the probability of success for a given plan, given the resident attributes.

By comparing the actual recovery score 245 (e.g., defined based on whether the resident actually recovered and/or how long recovery took) to the score generated by the machine learning model, the machine learning system can iteratively refine the model to generate more accurate recovery scores.

In at least one embodiment, the training data 250 can be used to train multiple models. For example, a first model may be trained to predict whether a given input goal is likely to be reached, and/or how long it will take to reach the goal, based to the resident attributes. A second model may be trained to predict whether a given input approach is likely to be successful and/or how long it will take the approach to work, based on resident attributes and goal(s). In this way, the machine learning system can use the first model to generate appropriate goal(s) for the resident, while the second model is used to generate appropriate approaches to achieve those selected goal(s).

Similarly, in some embodiments, separate models may be trained for each aspect of the recovery score 245. That is, a first model may be trained to predict the probability that a goal will be reached and/or that an approach will work, while a second model is trained to predict the time that will likely be needed to achieve the goal/for the approach to work. This may allow each model to learn to specialize to the specific needs of the particular task, enabling improved accuracy of the resulting care plans.

Example Workflow for Generating Care Plans Using Machine Learning

Figure 3:
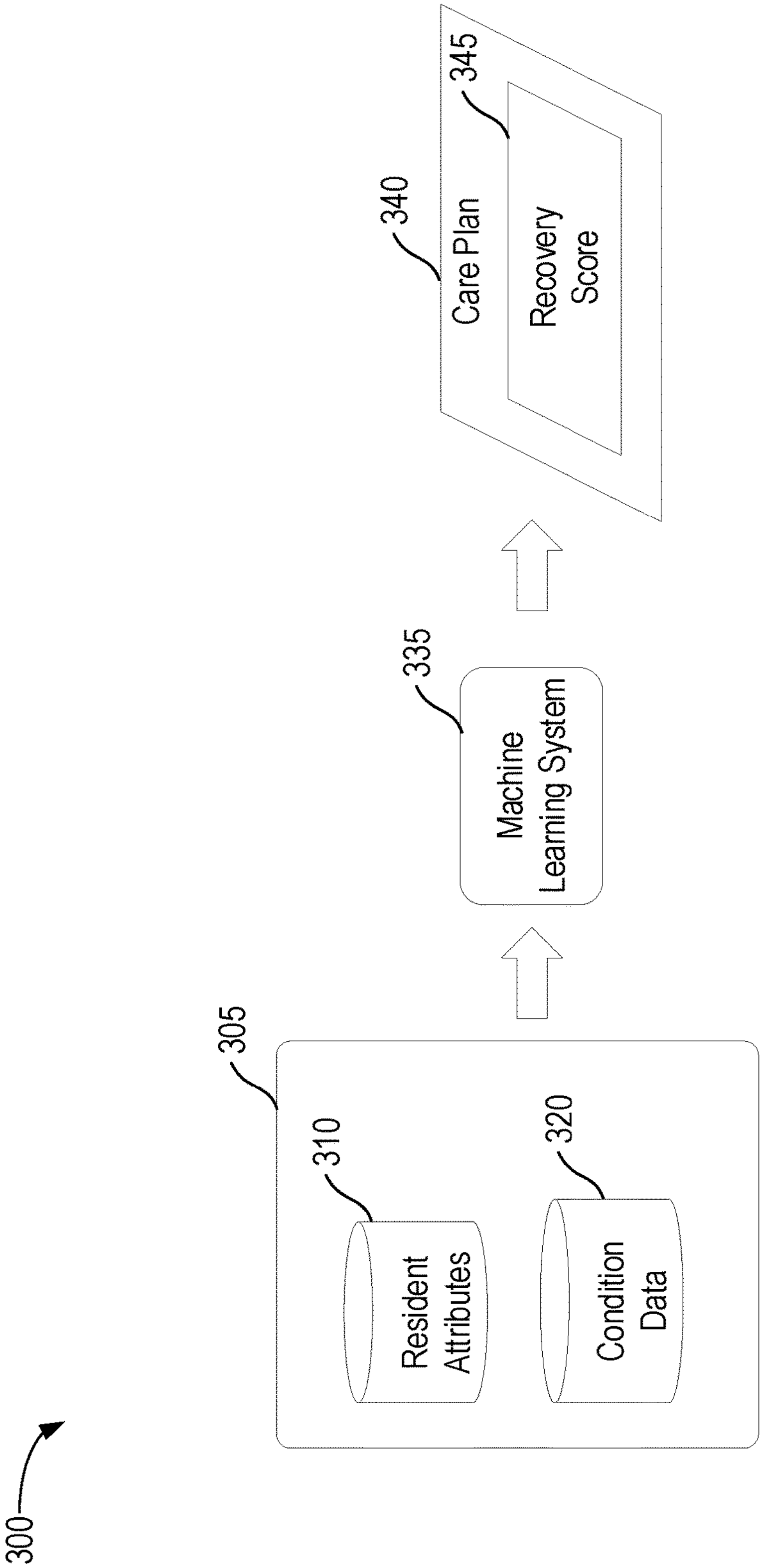
FIG. 3 depicts an example workflow for generating care plans and recovery scores using machine learning models.

FIG. 3 depicts an example workflow 300 for generating care plans and recovery scores using machine learning models. In some embodiments, the workflow 300 is performed using trained models, such as the machine learning models 140 of FIG. 1.

In the illustrated workflow 300, a set of resident data 305 is evaluated by a machine learning system 335 using one or more machine learning models (e.g., machine learning model 140 of FIG. 1) to generate and/or evaluate one or more care plan(s) 340, each with a corresponding recovery score 345. In embodiments, the machine learning system 335 may be implemented using hardware, software, or a combination of hardware and software. In some embodiments, the machine learning system 335 corresponds to the machine learning system 135 of FIG. 1, and/or the machine learning system 235 of FIG. 2. In other aspects, as discussed above, the machine learning system 335 may differ from the system that trained the model and/or generated the training data.

The resident data 305 generally includes data or information associated with one or more residents (also referred to as patients or users). That is, the resident data 305 may include, for one or more residents, a set of one or more snapshots of the resident characteristics or attributes at one or more points in time. For example, the resident data 305 may include information relating to a set of residents residing in one or more long-term care facilities. The resident data 305 may generally be stored in any suitable location. For example, the resident data 305 may be stored within the machine learning system 335, or may be stored in one or more remote repositories, such as in a cloud storage system. In at least one embodiment, the resident data 305 is distributed across multiple data stores.

In the illustrated example, the resident data 305 includes, for each resident reflected in the data, a set of one or more resident attributes 310 and condition data 320. In some embodiments, as discussed above, the data contained within the resident attributes 310 and condition data 320 are associated with timestamps or other indications of the relevant time or period for the data. In this way, the machine learning system 335 can generate a corresponding care plan 340 based on the relevant attributes 310 and conditions 320 at a given time.

As discussed above, the resident attributes 310 generally include information relating to a set of one or more specified features, attributes, or characteristics describing the resident(s) (such as fall risk, depression risk, acuity score, demographic data, and the like), and the condition data 320 generally corresponds to information relating to a set of specified assessments, problems, conditions, disorders, or issues relating to the functional state of the resident.

Although the illustrated resident data 305 includes several discrete components for conceptual clarity, in some embodiments, the resident data 305 used by the machine learning system 335 may include fewer components (e.g., a subset of the illustrated examples) or additional components not depicted. Additionally, though the illustrated example provides general groupings of attributes to aid understanding (e.g., grouping attributes and conditions), in some embodiments, the resident data 305 may be represented using any number of groups. That is, the individual attributes may simply be used as input to the machine learning system 335, without reference to any larger grouping or component.

Additionally, though the above discussion relates to receiving specified sets of data (e.g., specified diagnoses or other attributes), in some aspects, the machine learning system 335 may receive a broader set of data (e.g., all diagnoses or attributes of the users) and select which subset of the data to consider (e.g., based on the features specified in the machine learning model).

In the illustrated example, the resident data 305 is used to generate one or more care plans 340, each with a corresponding recovery score 345. As discussed above, the care plans 340 can generally indicate a set of details for how clinicians, caregivers, nurses, doctors, or other users should treat or otherwise respond to each condition of the resident. For example, for each problem reflected in the condition data 320, the care plans 340 may indicate one or more goals such as partial or total amelioration of the problem, as well as one or more approaches to achieve that goal.

In at least one embodiment, the machine learning system 335 generates the care plans 340 and recovery scores 345 by processing a variety of alternatives (sequentially or in parallel). For example, for each of a defined set of possible goals for a given condition, the machine learning system 335 may generate a corresponding score indicating the suitability of the goal. Similarly, for each of a defined set of possible approaches to achieve a goal or remediate an issue, the machine learning system 335 can generate a corresponding score indicating the likely efficacy of the approach. These score(s) can then be used to define the recovery score 345 for each alternative care plan 340.

As discussed above, the machine learning system 335 can generate the recovery scores 345 by identifying or extracting the relevant attributes from the resident data 305 (e.g., the relevant diagnoses, as indicated by the machine learning model), receiving an indication of the proposed care plan, and processing these attributes using the weights and architecture of the machine learning model to generate an overall recovery score 345 for the user based on the attributes and plan. In some embodiments, the recovery scores 345 can additionally or alternatively include a classification or category, such as a low, moderate, or high probability of success, or a short-term, medium-term, or long-term expected duration of the care plan, determined based on one or more threshold values for the recovery scores.

In at least one embodiment, the alternative plans can be ranked and/or filtered based on the recovery scores 345, and one or more top-scored care plans 340 can be selected. These top plans may be suggested or recommended to a user (e.g., output to a clinician via a graphical user interface (GUI)), automatically initiated, and the like.

In some embodiments, the machine learning system 335 can generate a new recovery score 345 and/or care plan 340 for each resident periodically (e.g., daily). In some embodiments, the machine learning system 335 generates a new care plan 340 and recovery score 345 whenever new data becomes available (or when the resident data 305 changes). For example, when a new issue is reported for a resident, the machine learning system 335 may use their current attributes to generate an optimized care plan 340. As another example, whenever a resident's attributes change (e.g., due to a newly-received diagnosis and/or a removed diagnosis), the machine learning system 335 may automatically detect the change and generate an updated care plan 340 that is specifically-tailored to the individual resident at the specific time. This targeted prophylactic treatment can significantly improve resident conditions and reduce the burden on caregivers.

Advantageously, the automatically generated care plans 340 and recovery scores 345 can significantly improve the outcomes of the residents, helping to identify optimal treatment options, thereby preventing further deterioration and significantly reducing harm. Additionally, the autonomous nature of the machine learning system 335 enables improved computational efficiency and accuracy, as the recovery scores 345 and/or care plans 340 are generated objectively (as opposed to the subjective judgment of clinicians or other users), as well as quickly and with minimal computational expense. That is, as the scores and plans can be automatically updated whenever new data is available, users need not manually retrieve and review the relevant data (which incurs wasted computational expense, as well as wasted time for the user).

Further, in some embodiments, the machine learning system 335 can regenerate care plans 340 and/or recovery scores 345 during specified times (e.g., off-peak hours, such as overnight) to provide improved load balancing on the underlying computational systems. For example, rather than requiring caregivers to retrieve and review resident data for a facility each morning to determine if anything occurred overnight or the previous day that may require a new care plan, the machine learning system 335 can automatically identify such changes, and use the machine learning model(s) to regenerate care plans 340 and recovery scores 345 before the shift begins. This can transfer the computational burden, which may include both processing power of the storage repositories and access terminals, as well as bandwidth over one or more networks, to off-peak times, thereby reducing congestion on the system during ordinary (e.g., daytime) use and taking advantage of extra resources that are available during the non-peak (e.g., overnight) hours.

In these ways, embodiments of the present disclosure can significantly improve resident outcomes while simultaneously improving the operations of the computers and/or networks themselves (at least through improved and more accurate scores and plans, as well as better load balancing of the computational burdens).

Example Workflow for Refining Machine Learning Models

Figure 4:
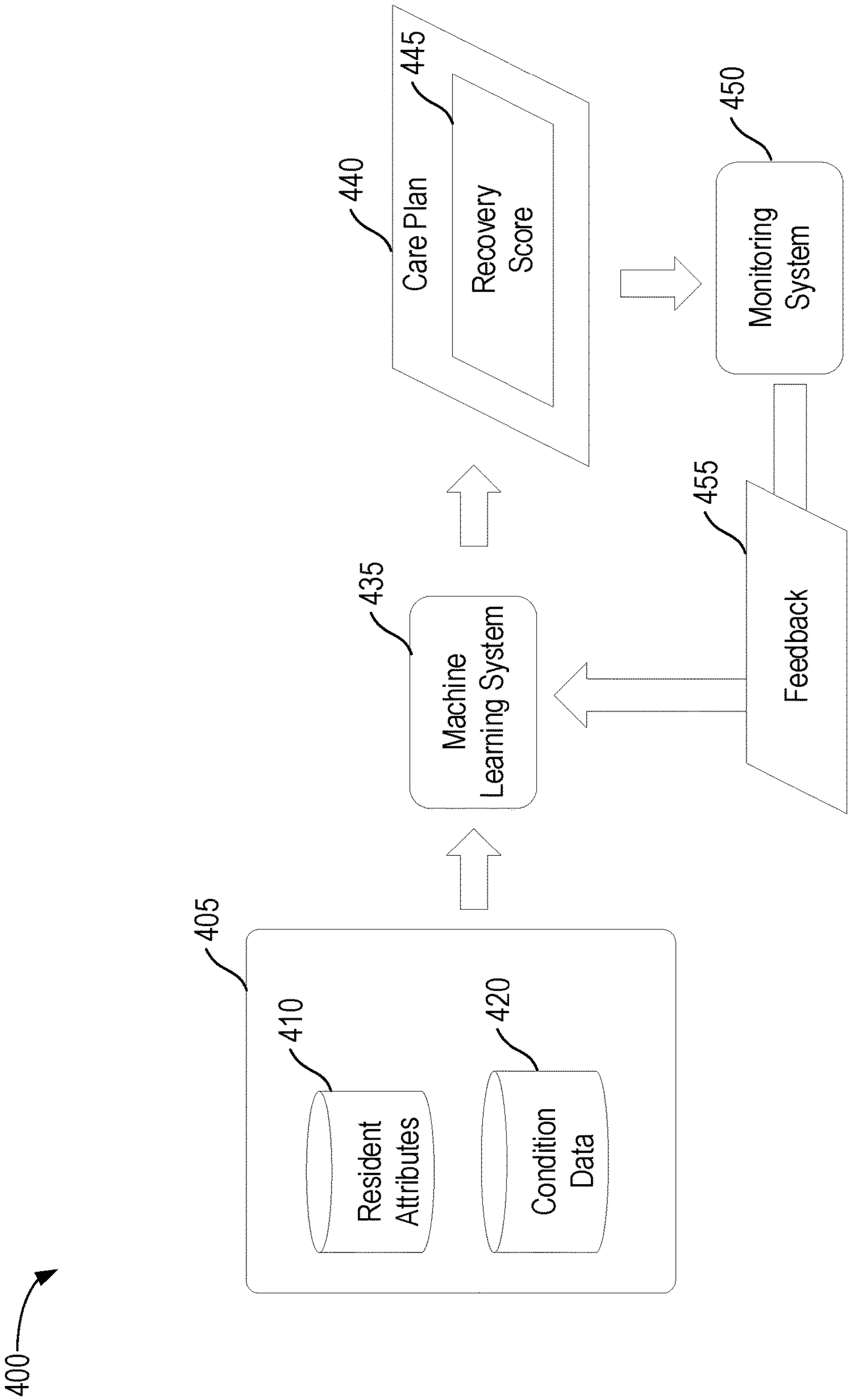
FIG. 4 depicts an example workflow for refining machine learning models to generate and evaluate care plans.

FIG. 4 depicts an example workflow for refining machine learning models to generate and evaluate care plans. In some embodiments, the workflow 400 is performed using trained models, such as the machine learning models 140 of FIG. 1.

The depicted workflow 400 differs from the workflow 300 of FIG. 3 in that it enables online refinement of the machine learning models based on updated information, thereby ensuring that the models can dynamically create optimized plans even when general conditions change. In the illustrated workflow 400, a set of resident data 405 is evaluated by a machine learning system 435 using one or more machine learning models (e.g., machine learning model 140 of FIG. 1) to generate and/or evaluate one or more care plan(s) 440, each with a corresponding recovery score 445. In embodiments, the machine learning system 435 may be implemented using hardware, software, or a combination of hardware and software. In some embodiments, the machine learning system 435 corresponds to the machine learning system 135 of FIG. 1, the machine learning system 235 of FIG. 2, the machine learning system 335 of FIG. 3. In other aspects, as discussed above, the machine learning system 435 may differ from the system that trained the model and/or generated the training data.

In some embodiments, the workflow 400 generally mirrors the workflow 300 of FIG. 3 to generate the care plans 440 and recovery scores 445. As discussed above, the resident data 405 generally includes data or information associated with one or more residents (also referred to as patients or users). That is, the resident data 405 may include, for one or more residents, a set of one or more snapshots of the resident characteristics or attributes at one or more points in time. For example, the resident data 405 may include information relating to a set of residents residing in one or more long-term care facilities. The resident data 405 may generally be stored in any suitable location. For example, the resident data 405 may be stored within the machine learning system 435, or may be stored in one or more remote repositories, such as in a cloud storage system. In at least one embodiment, the resident data 405 is distributed across multiple data stores.

In the illustrated example, the resident data 405 includes, for each resident reflected in the data, a set of one or more resident attributes 410 and condition data 420. In some embodiments, as discussed above, the data contained within the resident attributes 410 and condition data 420 are associated with timestamps or other indications of the relevant time or period for the data. In this way, the machine learning system 435 can generate a corresponding care plan 440 based on the relevant attributes 410 and conditions 420 at a given time.

As discussed above, the resident attributes 410 generally include information relating to a set of one or more specified features, attributes, or characteristics describing the resident(s) (such as fall risk, depression risk, acuity score, demographic data, and the like), and the condition data 420 generally corresponds to information relating to a set of specified assessments, problems, conditions, disorders, or issues relating to the functional state of the resident.

Although the illustrated resident data 405 includes several discrete components for conceptual clarity, in some embodiments, the resident data 405 used by the machine learning system 435 may include fewer components (e.g., a subset of the illustrated examples) or additional components not depicted. Additionally, though the illustrated example provides general groupings of attributes to aid understanding (e.g., grouping attributes and conditions), in some embodiments, the resident data 405 may be represented using any number of groups. That is, the individual attributes may simply be used as input to the machine learning system 435, without reference to any larger grouping or component.

Additionally, though the above discussion relates to receiving specified sets of data (e.g., specified diagnoses or other attributes), in some aspects, the machine learning system 435 may receive a broader set of data (e.g., all diagnoses or attributes of the users) and select which subset of the data to consider (e.g., based on the features specified in the machine learning model).

In the illustrated example, the resident data 405 is used to generate one or more care plans 440, each with a corresponding recovery score 445. As discussed above, the care plans 440 can generally indicate a set of details for how clinicians, caregivers, nurses, doctors, or other users should treat or otherwise respond to each condition of the resident. For example, for each problem reflected in the condition data 420, the care plans 440 may indicate one or more goals such as partial or total amelioration of the problem, as well as one or more approaches to achieve that goal.

In at least one embodiment, the machine learning system 435 generates the care plans 440 and recovery scores 445 by processing a variety of alternatives (sequentially or in parallel). For example, for each of a defined set of possible goals for a given condition, the machine learning system 435 may generate a corresponding score indicating the suitability of the goal. Similarly, for each of a defined set of possible approaches to achieve a goal or remediate an issue, the machine learning system 435 can generate a corresponding score indicating the likely efficacy of the approach. These score(s) can then be used to define the recovery score 445 for each alternative care plan 440.

As discussed above, the machine learning system 435 can generate the recovery scores 445 by identifying or extracting the relevant attributes from the resident data 405 (e.g., the relevant diagnoses, as indicated by the machine learning model), receiving an indication of the proposed care plan, and processing these attributes using the weights and architecture of the machine learning model to generate an overall recovery score 445 for the user based on the attributes and plan. In some embodiments, the recovery scores 445 can additionally or alternatively include a classification or category, such as a low, moderate, or high probability of success, or a short-term, medium-term, or long-term expected duration of the care plan, determined based on one or more threshold values for the recovery scores.

In at least one embodiment, the alternative plans can be ranked and/or filtered based on the recovery scores 445, and one or more top-scored care plans 440 can be selected. These top plans may be suggested or recommended to a user (e.g., output to a clinician via a GUI), automatically initiated, and the like.

In some embodiments, the machine learning system 435 can generate a new recovery score 445 and/or care plan 440 for each resident periodically (e.g., daily). In some embodiments, the machine learning system 435 generates a new care plan 440 and recovery score 445 whenever new data becomes available (or when the resident data 405 changes). For example, when a new issue is reported for a resident, the machine learning system 435 may use their current attributes to generate an optimized care plan 440. As another example, whenever a resident's attributes change (e.g., due to a newly-received diagnosis and/or a removed diagnosis), the machine learning system 435 may automatically detect the change and generate an updated care plan 440 that is specifically-tailored to the individual resident at the specific time. This targeted prophylactic treatment can significantly improve resident conditions and reduce the burden on caregivers.

Advantageously, the automatically generated care plans 440 and recovery scores 445 can significantly improve the outcomes of the residents, helping to identify optimal treatment options, thereby preventing further deterioration and significantly reducing harm. Additionally, the autonomous nature of the machine learning system 435 enables improved computational efficiency and accuracy, as the recovery scores 445 and/or care plans 440 are generated objectively (as opposed to the subjective judgment of clinicians or other users), as well as quickly and with minimal computational expense. That is, as the scores and plans can be automatically updated whenever new data is available, users need not manually retrieve and review the relevant data (which incurs wasted computational expense, as well as wasted time for the user).

Further, in some embodiments, the machine learning system 435 can regenerate care plans 440 and/or recovery scores 445 during specified times (e.g., off-peak hours, such as overnight) to provide improved load balancing on the underlying computational systems. For example, rather than requiring caregivers to retrieve and review resident data for a facility each morning to determine if anything occurred overnight or the previous day that may require a new care plan, the machine learning system 435 can automatically identify such changes, and use the machine learning model(s) to regenerate care plans 440 and recovery scores 445 before the shift begins. This can transfer the computational burden, which may include both processing power of the storage repositories and access terminals, as well as bandwidth over one or more networks, to off-peak times, thereby reducing congestion on the system during ordinary (e.g., daytime) use and taking advantage of extra resources that are available during the non-peak (e.g., overnight) hours.

In the illustrated workflow 400, once a care plan 440 have been implemented (e.g., once it has been selected or approved by a clinician), the monitoring system 450 can evaluate its efficacy in real-time (or near real-time). For example, the monitoring system 450 may periodically or continuous evaluate the resident data 405 (e.g., the condition data 420) to determine whether any condition(s) have changed. In at least one embodiment, while performing the care plan (e.g., providing therapy, medications, assessments, and the like), clinicians or caregivers can note the resident's progress, such as via natural language notes, or by selecting options (e.g., from a drop down or radio button in a GUI) indicating the status of the resident and/or conditions. Although depicted as a discrete system for conceptual clarity, in embodiments, the monitoring system 450 may be implemented as a standalone service, or as part of the machine learning system 435 (or another system).

In the illustrated workflow, the monitoring system 450 generates feedback 455 based on the monitored care plan(s) 440. In one embodiment, the monitoring system 450 can receive explicit update from users (e.g., clinicians) indicating whether the care plan is working. In some embodiments, the monitoring system 450 generates new feedback 445 each time the condition of a resident changes. For example, if the resident data 405 indicates that a given condition has improved or has been remediated (e.g., pain is reduced), the monitoring system 450 may generate feedback 455 indicating the corresponding care plan being used for the resident, the portion(s) of the care plan that may be responsible for the change, how long the change took to occur, and the like. Similarly, if the monitoring system 450 determines that the condition has worsened, the feedback 455 can similarly indicate the corresponding care plan, approach(es), and/or timeline.

In at least one embodiment, the monitoring system 450 may also generate feedback 455 indicating that a resident condition has not changed. For example, if the resident data 405 indicates that a given condition has remained the same for a threshold period of time (e.g., no change for a week, a month, and the like), the monitoring system 450 can generate feedback 455 indicating that the current care plan, though not harming the resident, does not appear to be helping them recover. In some embodiments, the threshold time used may be specified based on the underlying condition, and/or may be determined based on the timeline indicated in the care plan. For example, if the care plan indicates a goal of partial remediation within a month, the monitoring system 450 may determine that the care plan has failed once one month has passed.

In the illustrated workflow 400, the machine learning system 435 uses the feedback 455 to refine the machine learning model(s) used to generate and/or score care plans. For example, if the feedback 455 indicates that a specific resident has recovered from a given condition, the machine learning system 435 may use the resident's attributes, along with the current care plan for the resident's condition, as input to the model in order to generate a new recovery score 445 for the plan. The machine learning system 435 can then compare this generated score to the ground-truth (e.g., based on the newly-learned fact that the care plan worked), and use the resulting difference to refine the machine learning model(s). In this way, the machine learning system 435 can learn to generate better and more accurate care plans 440 and recovery score 445 for future conditions.

In some embodiments, as discussed above, the machine learning system 435 may perform this model refinement whenever new feedback 455 is received. In other embodiments, the machine learning system 435 may defer the refinement until specified hours (e.g., overnight, or during non-peak times) to reduce the computational burden of the refinement. In one such embodiment, the machine learning system 435 (or another system) can store the feedback 455 to be periodically used during such defined times.

Example Graphical User Interface for Machine Learning-Based Care Planning

Figure 5:
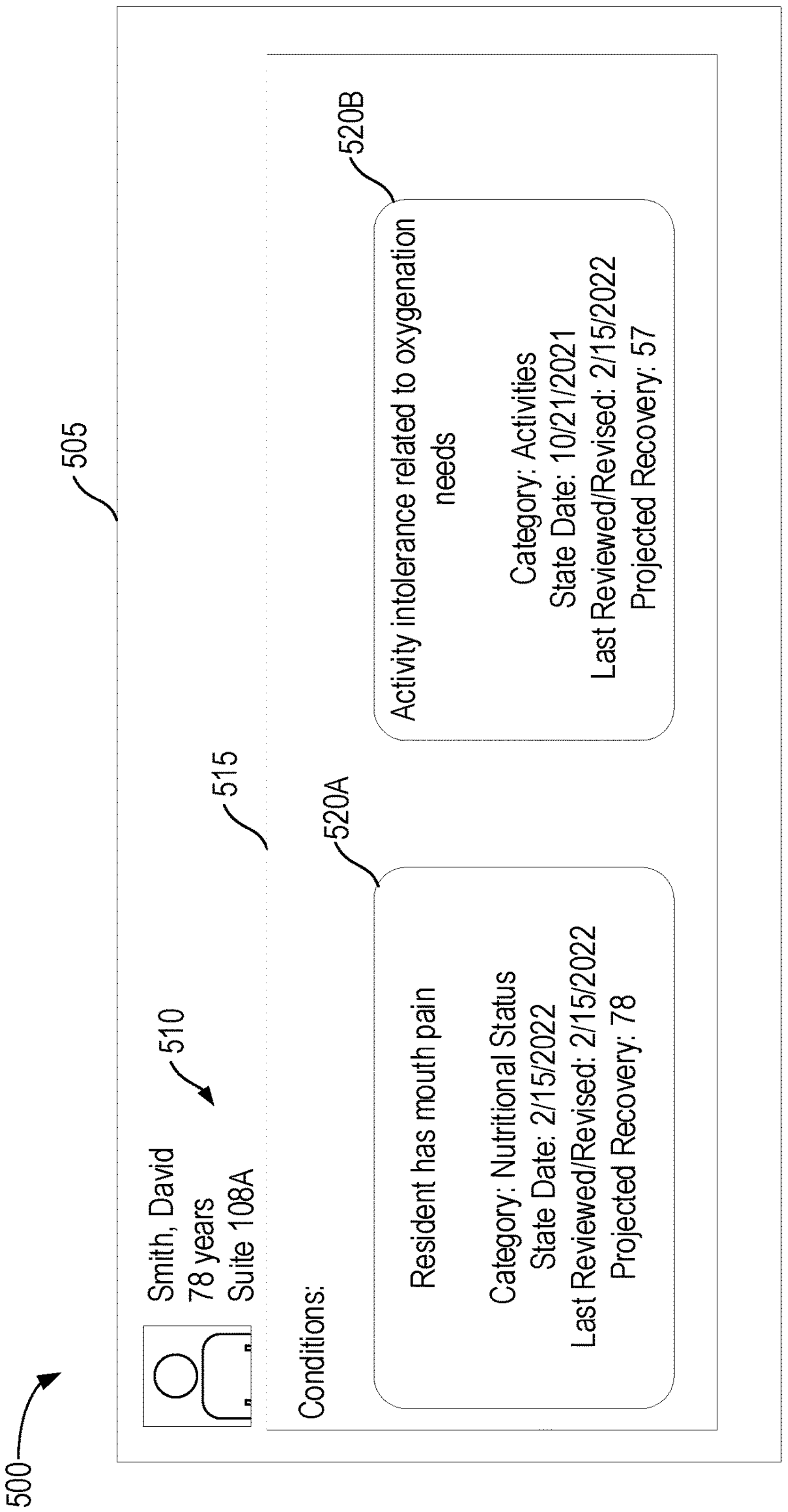
FIG. 5 depicts a graphical user interface for using machine learning to generate and review care plans.

FIG. 5 depicts a graphical user interface (GUI) 500 for using machine learning to generate and review care plans. In embodiments, users may access the GUI 500 using a variety of devices, including desktop computers, laptop computers, tablets, smartphones, access terminals in a residential facility, and the like.

The illustrated GUI 500 depicts a resident profile 505 for a resident in a residential facility (e.g., a long-term care facility such as a nursing home). Although the illustrated example depicts a resident profile, the GUI 500 can similarly display user data for a variety of individuals, including non-resident patients or other users. In the illustrated example, the resident profile 505 includes a first portion 510 for biographical data, including a picture of the resident, the resident's name, the resident's age, the assigned room or suite where the resident resides, and the like. In embodiments, other data (including more attributes not included in the illustrated example, as well as fewer attributes) may be displayed depending on the particular implementation.

In the illustrated example, the resident profile 505 also includes a portion 515 that lists various conditions, issues, problems, or disorders of the resident. The conditions may generally be self-reported (e.g., reported by the resident), reported by a clinician or caregiver, and the like. In the illustrated example, the resident has a first condition 520A corresponding to mouth pain (e.g., due to cavities, infection, or other concerns), and a second condition 520B corresponding to activity intolerance due to oxygenation needs (e.g., due to poor oxygen uptake or circulation).

As illustrated, each condition 520 further indicates a variety of related context, such as the category of the condition, the date on which the condition started or was first reported, the date on which the care plan associated with the condition was last reviewed (e.g., affirmed by a user) or revised, and the projected recovery score for the condition.

In an embodiment, the projected recovery may be determined using one or more machine learning models, as discussed above. For example, a machine learning system (e.g., machine learning system 335 of FIG. 3 and/or machine learning system 435 of FIG. 4) may process the resident's attributes and the care plan to generate a recovery score indicating the probability that the resident will recover from the condition, the predicted duration of the condition until recovery, and the like.

In some embodiments, the projected recovery may be determined based further on the historical attributes of the particular resident. For example, in addition to computing a recovery score using a model trained on a wide variety of data, the machine learning system may further evaluate the specific resident's attributes to determine whether this care plan has already been attempted for the resident, how much time the resident has spent on the current care plan, how much time has elapsed since the condition began, and the like. In one such embodiment, if the resident has already (unsuccessfully) used a given care plan, if the user is currently on the care plan with no indications of recovery, or if the user has had the condition for a relatively long period of time, the machine learning system may reduce the recovery score to indicate that the specific care plan is less likely to succeed.

Although two conditions 520 are depicted, in embodiments, there may be any number of conditions associated with a given resident. Further, there may be a variety of other data available via the GUI 500. In some embodiments, the user is able to interact with the GUI, such as by tapping or clicking on a condition 520, to retrieve more information about the condition and care plan. One example of such interaction is described in below in more detail with reference to FIG. 6.

Example Graphical User Interface for Machine Learning to Generate Care Plans

Figure 6:
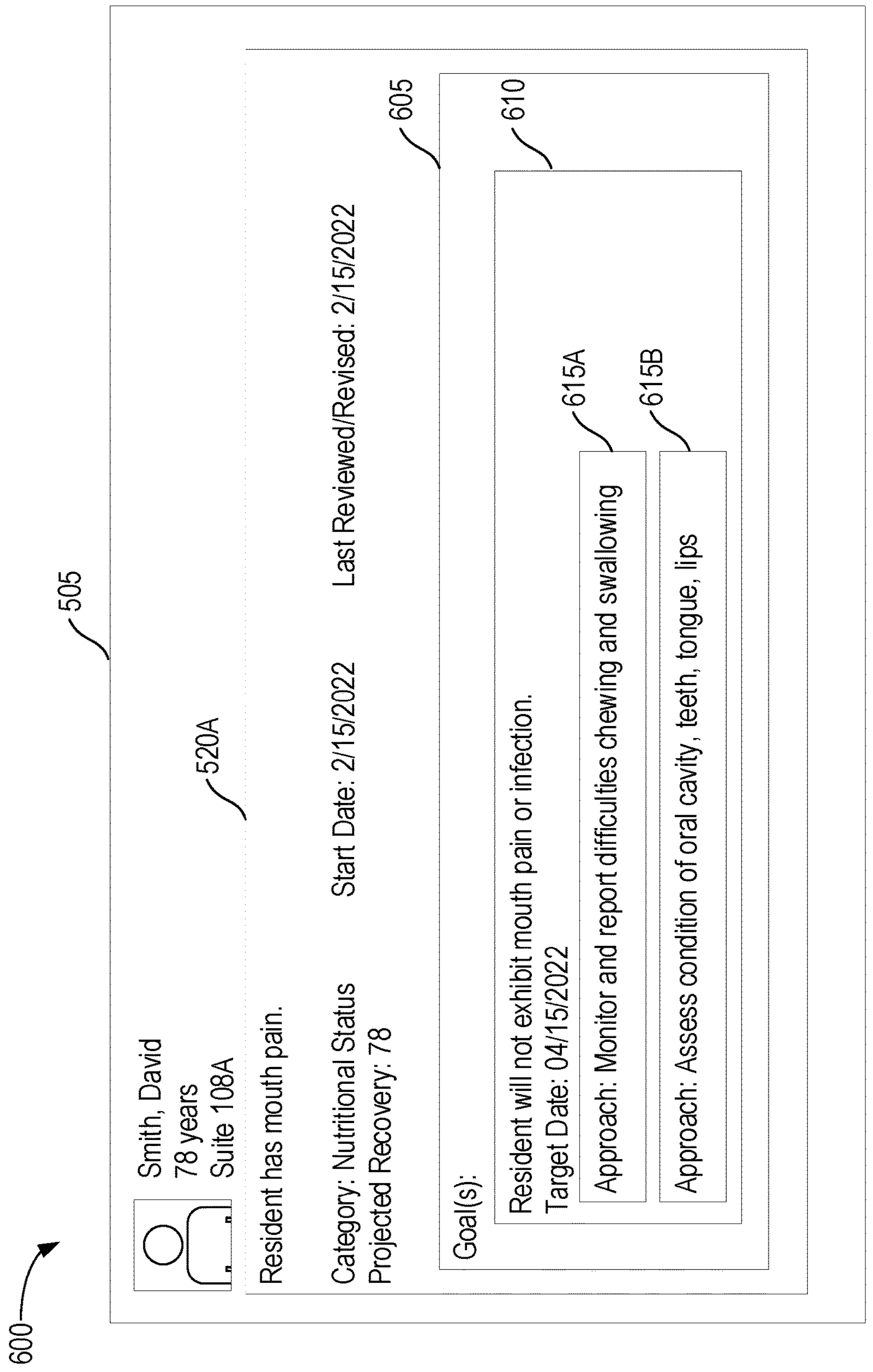
FIG. 6 depicts a graphical user interface for using machine learning to generate and review care plans.

FIG. 6 depicts a GUI 600 for using machine learning to generate and review care plans. In one embodiment, the GUI 600 corresponds to an interface provided when a user (e.g., a clinician) clicks, taps on, or otherwise selects one of the conditions indicated in the GUI 500 of FIG. 5.

In the illustrated example, the GUI 600 still depicts the resident profile 505, but has hidden the unselected condition 520B, and expanded the selected condition 520A. In the illustrated example, the GUI 600 includes a portion 605 indicating the goal(s) 610 associated with the selected condition. Although a single goal 610 is illustrated for conceptual clarity, there may be any number of goals depending on the particular implementation. For example, in at least one embodiment, the portion 605 may include a first goal for short-term goals (e.g., partial reduction in pain over the next week) and a second goal for long-term goals (such as complete elimination of the pain).

In some embodiments, as discussed above, the goal(s) 610 may be manually defined. For example, a clinician may select one or more goals based on reviewing the condition 520A and/or resident attributes. In some embodiments, some or all of the goal(s) 610 may be generated using machine learning. For example, as discussed above, the resident attributes and condition may be processed using a machine learning model trained to select or score goals based on their desirability to the resident (e.g., where reduced levels of pain are considered more desirable and therefore receive higher scores), based on their timelines (e.g., where sooner goals receive higher scores), and/or achievability (as determined by the machine learning model based on the resident attributes). For example, a goal that includes significant pain reduction in a short timeline may be scored highly, unless the model indicates that the resident is unlikely to meet the goal (as determined based on prior training).

In other embodiments, the machine learning system may simply predict achievability of the goal (based on resident attributes). The machine learning system may then sort the alternative goals based at least in part on these achievability scores, and allow a user to select among them. In at least one embodiment, the user may further sort or filter these goals such that short-term goals are near the top (e.g., allowing them to select the best option from among short-term goals), such that specific levels of condition remediation are near the top (e.g., allowing them to select the best option that results in at least 50% reduction), and the like.

As depicted, the goal 610 includes that the resident should have no mouth pain or infection, with a target date of April 15. In the illustrated example, the goal(s) 610 are each further associated with one or more approaches 615 to achieve the goal 610. Specifically, the illustrated example includes an approach 615A corresponding to periodic monitoring and assessment with respect to chewing and swallowing, and an approach 615B corresponding to assessments relating to the oral cavity, teeth, tongue, and lips of the resident.

Although not included in the illustrated example, in some embodiments some or all of the approaches 615 may include further context, such as a frequency of the approach (e.g., how often an assessment should be performed), a dosage (in the case of medication), and the like.

In an embodiment, by referring to the GUI 600, caregivers can rapidly review the care plan, estimate how likely it is to succeed, and implement the indicated treatments or interventions. As used herein, a "care plan" may correspond to a specific approach 615 (with a corresponding goal 610 and condition 520), to a set of approaches 615 to achieve a given goal 605 for a given condition 520, to a set of goals 605 (each with a set of approaches) for a given condition 520, and/or to a set of conditions 520 (each with corresponding goals and approaches) for a given resident.

In some embodiments, the user can use the GUIs 500 and/or 600 to revise the care plans. For example, if the user determines that a care plan is not working, the user may interact with the GUI to generate an alternative care plan. In at least one embodiment, the machine learning system can store one or more alternative care plans each time a new care plan is generated or selected. This can allow the user to select from among pre-generated and pre-scored plans if no resident attributes have changed, thereby reducing computational expense of using the machine learning models. Additionally, in at least one embodiment, each time the resident attribute(s) change, the machine learning system may automatically generate and/or evaluate one or more care plans. The system may then prompt the user to review and approve one or more of the plans (or to remain using the current plan).

Example Method for Training Machine Learning Models

Figure 7:
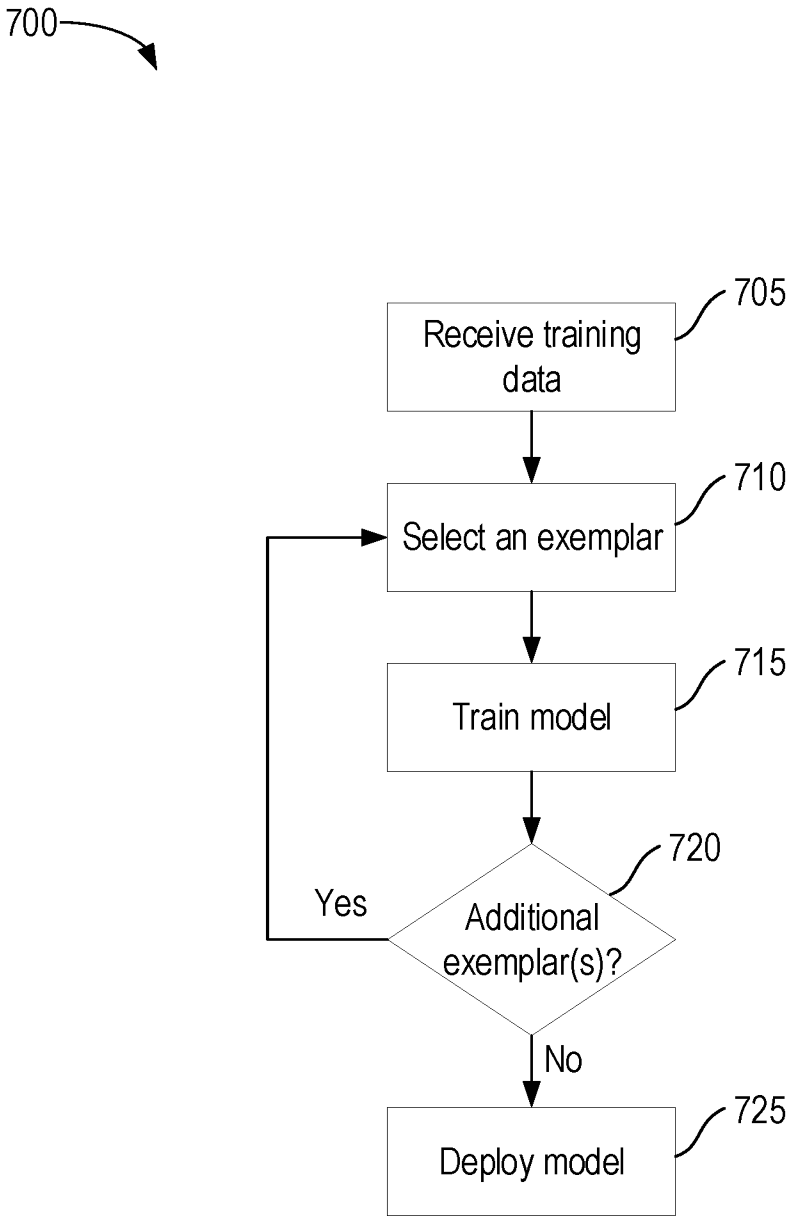
FIG. 7 is a flow diagram depicting an example method for training machine learning models to generate and evaluate care plans.

FIG. 7 is a flow diagram depicting an example method 500 for training machine learning models to generate and evaluate care plans. In the illustrated embodiment, the method 700 is performed by a machine learning system, such as the machine learning system 135 of FIG. 1. In other embodiments, the method 700 can be performed by other systems, such as dedicated training systems.

Figure 8:
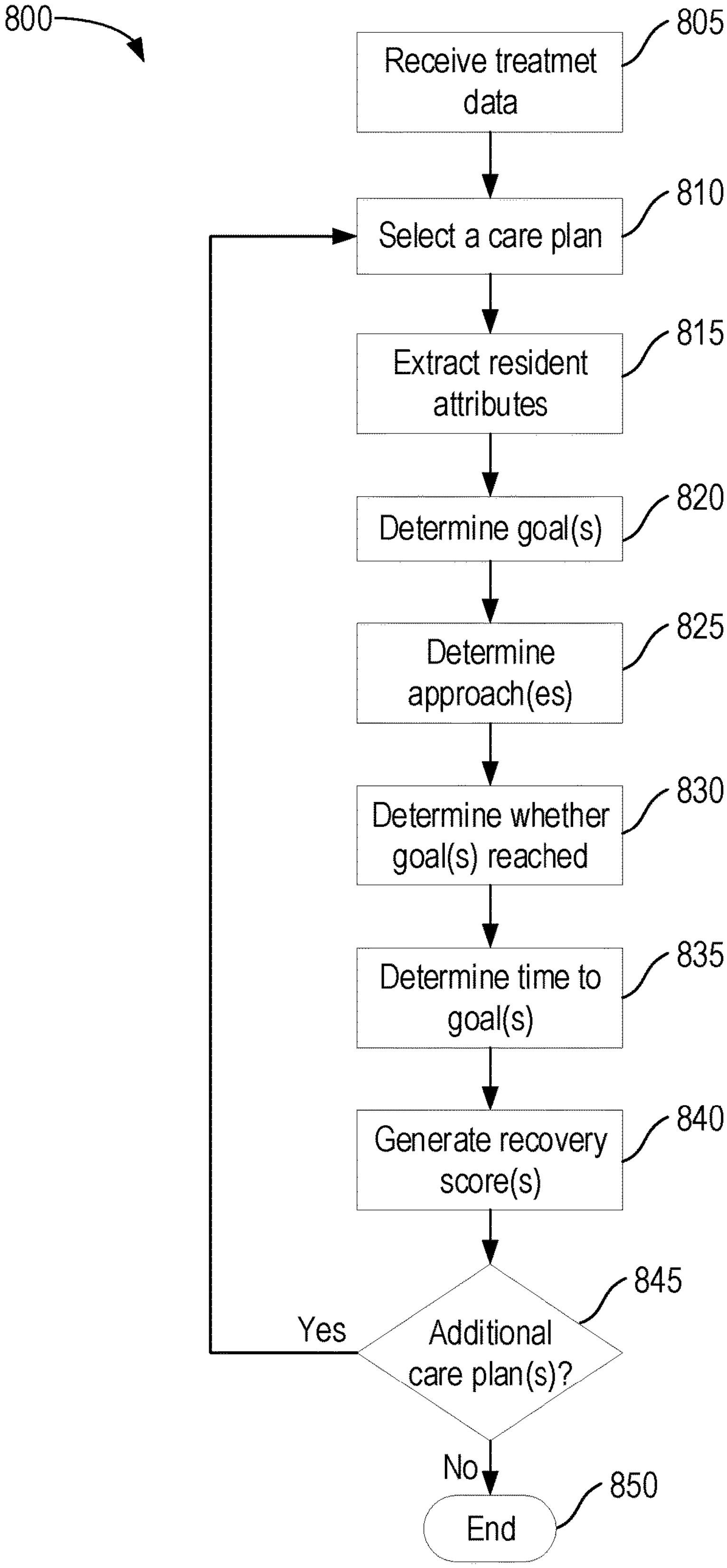
FIG. 8 is a flow diagram depicting an example method for generating training data for machine learning to evaluate care plans.

The method 700 begins at block 705, where the machine learning system receives training data (e.g., the training data generated using the workflow 200 of FIG. 2, and/or generated using the method 800 of FIG. 8). In embodiments, receiving the training data may include receiving it from one or more other systems (e.g., data aggregation or preprocessing systems), retrieving it from local or remote storage, and the like. In one embodiment, the training data can generally include multiple sets of resident attributes, where each set of resident attributes indicates the attributes or characteristics of a corresponding resident during at a point or window of time associated with the selection or use of a corresponding care plan (e.g., within a defined window, such as one month prior, six months prior, and the like).

At block 710, the machine learning system selects one of the exemplars included in the training data. As used herein, an exemplar refers to a set of attributes (e.g., corresponding to a defined or learned set of features) from a single resident, associated with a particular condition. For example, the attributes may correspond to those present during a defined point or window of time when the condition was present. As an example, the exemplar may include indications as to the resident fall risk, depression risk, and/or acuity score, the demographics of the user, whether the user had any specified diagnoses at the time, whether the user had been clinically assessed with one or more defined conditions during the window, medication(s) the user used or was prescribed or used during the window, and the like. In some embodiments, the exemplar further indicates the care plan used by the resident (e.g., selected by a clinician) at the point in time or during the window to treat the condition.

Generally, the exemplar may be selected using any suitable criteria (including randomly or pseudo-randomly), as the machine learning system will use all exemplars during the training process. Although the illustrated example depicts selecting exemplars sequentially for conceptual clarity, in embodiments, the machine learning system may select and/or process multiple exemplars in parallel.

At block 715, the machine learning system trains a machine learning model based on the selected exemplar. For example, the machine learning system may use the attributes and care plan indicated in the exemplar to generate an output recovery score or classification for the care plan, with respect to the resident. As discussed above, this recovery score can generally indicate the predicted efficacy of the care plan, such as the probability that the care plan will allow the resident to recover from the condition (or otherwise reach the goal(s) specified in the care plan), a predicted time that will pass before the recovery occurs (or until the goal(s) are reached), and the like. In one such embodiment, lower values may indicate a lower probability that the resident will reach the goals, while a higher value indicates that the resident is relatively more likely to reach the indicated goal(s).

During training, this score can then be compared against a ground-truth associated with the selected exemplar (e.g., an indication as to whether the resident did, in fact, recover or otherwise reach the goal(s) using the care plan). In some embodiments, this comparison includes determining how much time elapsed between the start of the care plan and the eventual recovery (or successful reaching of the goal(s)). Based on this comparison, the parameters of the machine learning model can be updated. For example, if the generated recovery score is relatively low but the resident did, in fact, recover completely using the care plan, the machine learning system may modify the parameters such that the attributes and care plan in the exemplar result in a larger recovery score being generated.

At block 720, the machine learning system determines whether at least one additional exemplar remains in the training data. If so, the method 700 returns to block 710. If not, the method 700 continues to block 725. Although the illustrated example depicts iteratively refining the model using individual exemplars (e.g., using stochastic gradient descent), in some embodiments, the machine learning system can refine the model based on multiple exemplars simultaneously (e.g., using batch gradient descent).

At block 725, the machine learning system deploys the trained machine learning model for runtime use. In embodiments, this may include deploying the model locally (e.g., for runtime use by the machine learning system) and/or to one or more remote systems. For example, the machine learning system may distribute the trained model to one or more downstream systems, each responsible for one or more residential facilities (e.g., to one or more servers associated with specific care facilities, where these servers may use the model to evaluate care plans for residents at the specific facility).

Example Method for Generating Training Data for Machine Learning

FIG. 8 is a flow diagram depicting an example method 800 for generating training data for machine learning to evaluate care plans. In the illustrated embodiment, the method 800 is performed by a machine learning system, such as the machine learning system 235 of FIG. 2. In other embodiments, the method 800 can be performed by other systems, such as training systems, data generation and/or aggregation systems, and the like.

At block 805, the machine learning system receives treatment data (e.g., historical data 205 of FIG. 2). In an embodiment, the received treatment data can generally include data or information associated with one or more residents (also referred to as patients or users) from one or more prior points in time. That is, the treatment data may include, for one or more residents, a set of care plan(s) used by the resident at one or more points in time, where each care plan is associated with a set of resident characteristics or attributes at the time. In some embodiments, the treatment data includes attributes for a set of residents residing in one or more long-term care facilities.

In some embodiments, the received treatment data includes resident data corresponding to a defined set of features to be used to generate a machine learning model to evaluate care plans. These features may include, for example, specified diagnoses, specified clinical assessments and/or conditions, specified medications, specified demographics, and the like. In some embodiments, the treatment data can include additional data beyond these features (e.g., information about all medications that one or more residents have been prescribed, regardless of the specific medications used in the machine learning model). In one such embodiment, the machine learning system can identify and extract the relevant attributes or data based on the indicated features used for the machine learning model. In other embodiments, the received treatment data may include only the specific data corresponding to the indicated features (e.g., another system may filter the treatment data based on the features, thereby protecting data that is not needed to build the model).

In some embodiments, the treatment data can include one or more indications, for each care plan reflected in the data, as to whether the care plan was successful (e.g., the goal(s) were reached), the time that elapsed on the care plan until the goal(s) were reached, and the like.

At block 810, the machine learning system selects one of the care plans reflected in the treatment data. Generally, this selection can be performed using any suitable technique (including randomly or pseudo-randomly), as all of the care plans will be evaluated during the method 800. Although the illustrated example depicts an iterative or sequential selection and evaluation of each care plan, in some aspects, some or all of the method 800 may be performed in parallel. For example, rather than selecting and evaluating the data for each care plan individually, the machine learning system may process the data from some or all care plans sequentially or in parallel.

At block 815, the machine learning system extracts a set of resident attributes associated with the selected care plan. For example, the machine learning system may extract relevant attributes corresponding to a defined window of time prior to the start of the care plan (e.g., in the month leading up to the selection of the plan). This can allow the machine learning system to generate a training data set that indicates sets of attributes that immediately-preceded selection of the care plan by a clinician. As discussed above, the attribute extraction may generally include extracting data relating to characteristics of the resident that may impact the efficacy or success of the care plan, such as fall risk, depression risk, the resident's acuity score, demographics, diagnoses, clinical assessments, medications, and the like.

At block 820, the machine learning system determines the goal(s) specified in the selected care plan. Similarly, at block 825, the machine learning system determines the approach(es) specified for each goal. In some embodiments, as discussed above, the machine learning system can generate a training data set that enables a model to be trained to predict, generate, or score such goals and/or approaches (which may include training multiple models).

At block 830, the machine learning system determines whether any of the identified goal(s) were reached or achieved. For example, the treatment data may include indications (e.g., provided by the resident or a user) as to whether a given goal was reached using the selected care plan.

At block 835, the machine learning system can further determine how much time elapsed to reach any goal(s) that were achieved. That is, for each goal that was successfully reached, the machine learning system may determine the amount of time that elapsed between the start of the care plan and the time when the goal was reached (e.g., at the end of the care plan).

At block 840, based on this data, the machine learning system can generate one or more recovery scores for the selected care plan. In one embodiment, the recovery score is generated or assigned by a user. In some embodiments, the machine learning system uses an algorithmic or rules-based approach to define the recovery scores. In one embodiment, care plans where all of the goal(s) were successfully reached may receive relatively higher scores, as compared to care plans where only a subset of the goals were reached, or where no goals were reached. In some embodiments, care plans where the condition improved (even if the goals were not reached) may be scored more highly, as compared to care plans where the condition stayed the same, which may in turn be scored more highly than care plans where the condition worsened. Further, in some embodiments, the generated recovery score may be inversely related to the time needed to reach the goal, such that shorter timelines result in higher scores, as compared to long timelines.

In some embodiments, as discussed above, the machine learning system may generate multiple recovery scores (or a recovery score having multiple components) for the care plan. For example, a first value or set of values may indicate whether each specific goal was reached, allowing a model to be trained to predict the achievability of each goal (e.g., the probability that each goal will be reached, given the resident attributes). A second value or set of values may indicate whether each specific approach succeeded, allowing a model to be trained to predict the probability that the resident will recover. A third value or set of values may indicate the time that elapsed until the goal was reached, allowing a model to be trained to predict how much time will be needed for the resident to recover.

In this way, the machine learning system can build a training set that includes relevant attributes which affected the efficacy of various care plans. This data can be used to train one or more machine learning models, as discussed above and in more detail below, to predict the probability that a given care plan will work for a specific resident, the time that will be needed, and the like.

At block 845, the machine learning system determines whether at least one additional care plan reflected in the treatment data has not been evaluated. If so, the method 800 returns to block 810. If not (e.g., if all care plans reflected in the treatment data have been evaluated), the method 800 terminates at block 850.

In some embodiments, the method 800 can be used periodically or upon other specified criteria (e.g., upon being triggered by a user or clinician) to generate or update training data used to train or refine one or more machine learning models. By iteratively using the method 800 (e.g., annually), the training data can be continuously or repeatedly updated, thereby allowing the machine learning system to refine the machine learning models to adjust to any changing conditions. This can significantly improve the accuracy and efficiency of such models.

Example Method for Generating Care Plans Using Machine Learning

Figure 9:
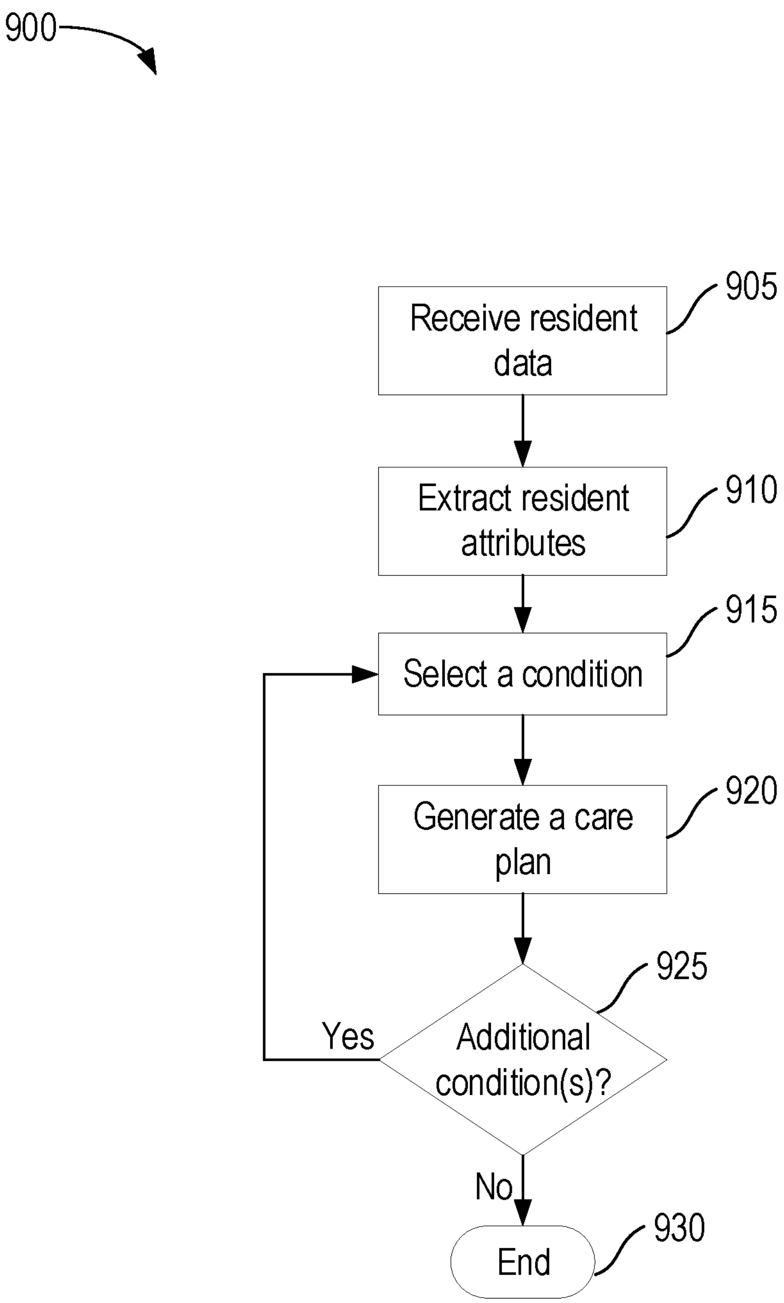
FIG. 9 is a flow diagram depicting an example method for generating care plans using machine learning models.

FIG. 9 is a flow diagram depicting an example method 900 for generating care plans using machine learning models. In the illustrated embodiment, the method 900 is performed by a machine learning system, such as the machine learning system 335 of FIG. 3 and/or the machine learning system 435 of FIG. 4. In other embodiments, the method 900 can be performed by other systems, such as dedicated inferencing systems.

At block 905, the machine learning system receives resident data (e.g., resident data 305 of FIG. 3). As discussed above, the resident data may include data or information associated with a resident (also referred to as a patient or a user in some aspects). In some embodiments, the resident data includes attributes for a resident residing in a long-term care facility.

In an embodiment, the resident data can generally include information relating to attributes of the resident, such as demographics of the resident, a set of one or more diagnoses of the resident, medications used by the resident, clinical assessments of condition(s) of the resident, current conditions or problems of the resident, and the like. In some embodiments, the received resident data corresponds to current information for the resident. That is, the resident data may be the most-recent data for each feature.

In at least one aspect, the resident data is received because a change has occurred. That is, the resident data may be provided to the machine learning system (e.g., using a push technique) based on determining that one or more of the attributes have changed since the last time the data was provided. In other embodiments, the machine learning system can retrieve or request the resident data, and evaluate it to determine whether any attributes have changed. In at least one embodiment, if no attributes have changed (with respect to the relevant features used by the model), the machine learning system can refrain from further processing of the data (e.g., refrain from generating a new care plan), thereby reducing computational expense.

Similarly, if the data is only provided upon detecting a change, the machine learning system need not review it at all, which also reduces computational expense of the system. Additionally, in some embodiments, the machine learning system can receive only the updated data (as opposed to receiving or retrieving the entirety of the resident data). That is, the storage systems may automatically transmit data when it is updated (or the machine learning system may request any new or changed data), enabling the care plan to be revised based on the new data without the need to re-transmit the older data. This, again, reduces the computational expense (including bandwidth, if the data is stored remotely from the machine learning system) of generating the scores.

In some embodiments, the received resident data includes data corresponding to a defined set of features that are used by the machine learning model. These features may include, for example, specific demographic data, specified diagnoses, specified clinical assessments and/or conditions, specified medications, and the like. In some embodiments, the resident data can include additional data beyond these features (e.g., information about all medications that the resident has been prescribed, regardless of the specific medications used in the machine learning model). In one such embodiment, the machine learning system can identify and extract the relevant attributes or data, based on the indicated features for the model. In other embodiments, the received resident data may include only the specific data corresponding to the indicated features (e.g., another system may filter the resident data based on the features, thereby protecting data that is not used by the model). In still another aspect, such unused features or attributes may simply be associated with a weight of zero in the model.

At block 910, the machine learning system extracts the set of relevant resident attributes, from the resident data, based on the specified features that are used by the machine learning model. That is, the machine learning system can extract, from the resident data, the relevant information for each feature. For example, if a specific diagnosis is included in the features, the machine learning system may search the resident data using one or more diagnosis codes (e.g., ICD-10 codes) corresponding to the specific diagnosis. If the resident currently has the diagnosis, it can be indicated in the corresponding resident attribute (e.g., with a value indicating the presence of the diagnosis). If the diagnosis is not found, this attribute may be set to a defined value, such as a null value or a value of zero, to indicate that the resident does not have the feature. As discussed above the attributes generally correspond to characteristics of the resident, such as a fall risk generated by one or more machine learning models, a depression risk generated by one or more machine learning models, an acuity score generated by one or more machine learning models, demographic data, and the like.

At block 915, the machine learning system selects one of the conditions of the resident reflected in the resident data. That is, the machine learning system can select one of the conditions, issues, or problems for which a care plan should be generated. In some embodiments, this includes selecting a condition that has changed (e.g., new conditions, improved conditions, worsened conditions, and the like). In some embodiments, this includes selecting a condition associated with an attribute that has changed (if some attributes are only used for some conditions). Generally, this selection can be performed using any technique (including randomly or pseudo-randomly), as the machine learning system will evaluate all of the resident's conditions during the method 900. Although an iterative or sequential process is depicted for conceptual clarity, in some embodiments, the machine learning system may evaluate some or all of the conditions in parallel.

At block 920, the machine learning system processes the identified/extracted attributes using a trained machine learning model to generate a care plan. As discussed above, the machine learning model may generally specify a set of parameters (e.g., weights) for input features and/or intermediate features (within internal portions of the model) learned during training. In some embodiments, as discussed above, the model may specify weights for individual features, for groups of features, or for both individual features and groups of features.

In some embodiments, as discussed above and in more detail below with reference to FIG. 10, the machine learning system may generate the care plan by scoring one or more options or alternative care plans using the model, allowing the highest-scored plan to be output as the generated plan.

At block 925, the machine learning system determines whether there is at least one additional condition for which a care plan is needed. If so, the method 900 returns to block 915. If not, the method 900 terminates at block 930.

In some embodiments, the machine learning system can optionally implements the selected care plan(s), output the care plan(s) to a user for approval, and the like.

Figure 10:
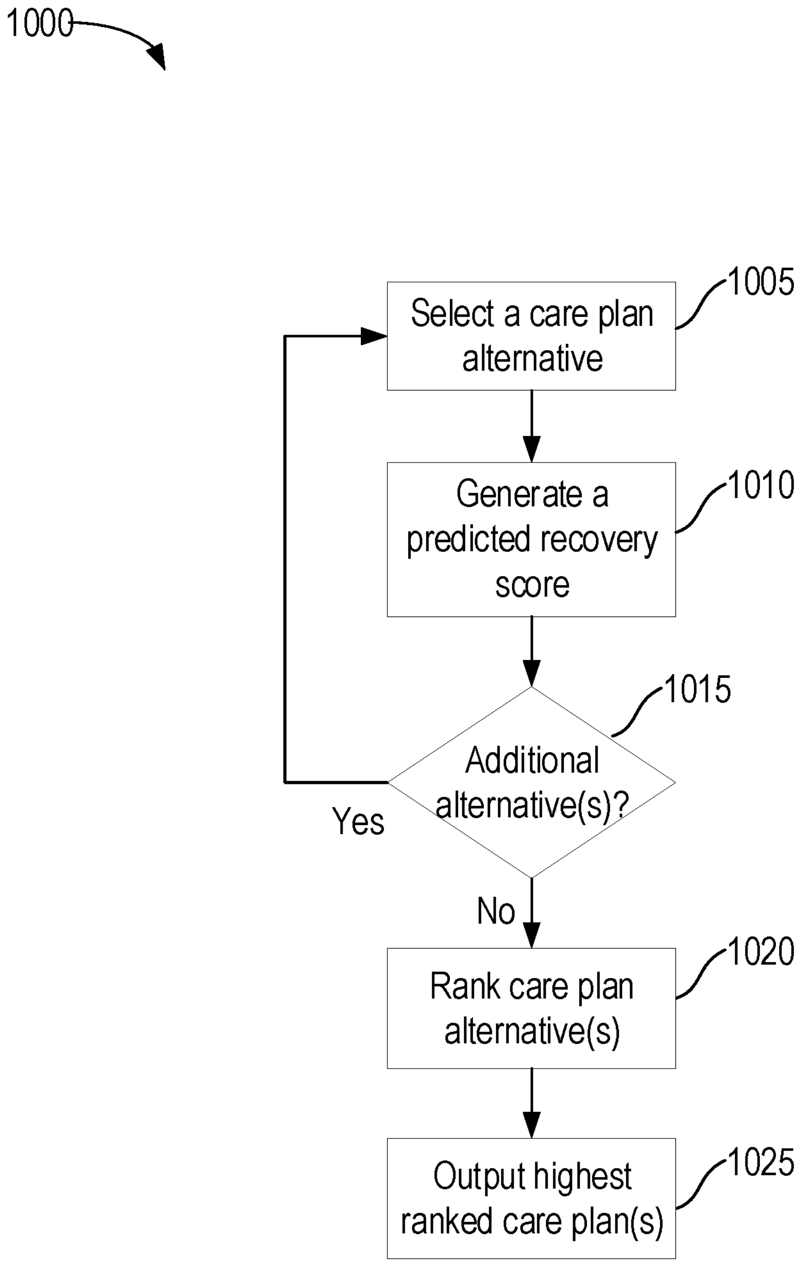
FIG. 10 is a flow diagram depicting an example method for evaluating care plan alternatives using machine learning.

Example Method for Using Machine Learning to Evaluate Care Plan Alternatives FIG. 10 is a flow diagram depicting an example method 1000 for evaluating care plan alternatives using machine learning. In the illustrated embodiment, the method 1000 is performed by a machine learning system, such as the machine learning system 335 of FIG. 3 and/or the machine learning system 435 of FIG. 4. In other embodiments, the method 1000 can be performed by other systems, such as dedicated inferencing systems. In one embodiment, the method 1000 provides additional detail for block 920 of FIG. 9.

At block 1005, the machine learning system selects a care plan alternative from a defined list of alternatives. For example, for each given condition, there may be a specified set of possible goal(s), and/or a specified set of possible approach(es) to reach the goal(s) and/or remediate or eliminate the condition. These alternatives may be specified, for example, by one or more users (e.g., clinicians, doctors, and the like) and/or in medical literature. In an embodiment, selecting a care plan alternative can include selecting one or more goal(s) for the specific condition being evaluated and/or selecting one or more approaches. Generally, this selection can be performed using any technique (including randomly or pseudo-randomly), as the machine learning system may evaluate each alternative or combination during the method 1000. Although an iterative or sequential process is depicted for conceptual clarity, in some embodiments, the machine learning system may evaluate some or all of the care plans in parallel.

At block 1010, the machine learning system generates a predicted recovery score for the selected care plan alternative. For example, as discussed above, the machine learning system may process the care plan, along with the resident's attributes (such as fall risk, depression risk, acuity score, demographic data, and the like), as input to a machine learning model trained to predict recovery for the resident if the care plan is followed. In some embodiments, as discussed above, this may include use of one or more models, and may include generating predictions relating to whether a given goal will be reached, whether a given approach will work, how much time will elapse before a goal is reached if a particular approach is used, and the like.

At block 1015, the machine learning system determines whether there is at least one additional care plan alternative that has not-yet been evaluated. If so, the method 1000 returns to block 1005. If not, the method 1000 continues to block 1020. Advantageously, the machine learning system can thereby enable a wide variety of care plans (including every possible combination of components, in some embodiments) to be considered for the resident. As there may be a large number of such combinations (e.g., thousands), the machine learning system can therefore enable caregivers to provide highly-tailored plans for the specific resident (which the caregiver could not otherwise do manually or mentally).

At block 1020, the machine learning system ranks the care plan alternatives based on the generated recovery scores. In some embodiments, the machine learning system can additionally or alternatively filter the care plan alternatives. For example, a user may indicate that they want to filter out any care plans with a recovery score below a defined threshold, with a timeline beyond a defined target date, with a goal that is insufficient (e.g., any care plans with a goal of less than a 50% reduction in pain), and the like.

At block 1025, the machine learning system then outputs one or more of the highest-ranked care plan alternatives, such as via the GUIs 500 and/or 600 of FIGS. 5 and 6. In this way, the user is able to rapidly review the alternative care plan options, selecting the plan that is most likely to result in beneficial results for the resident.

Figure 11:
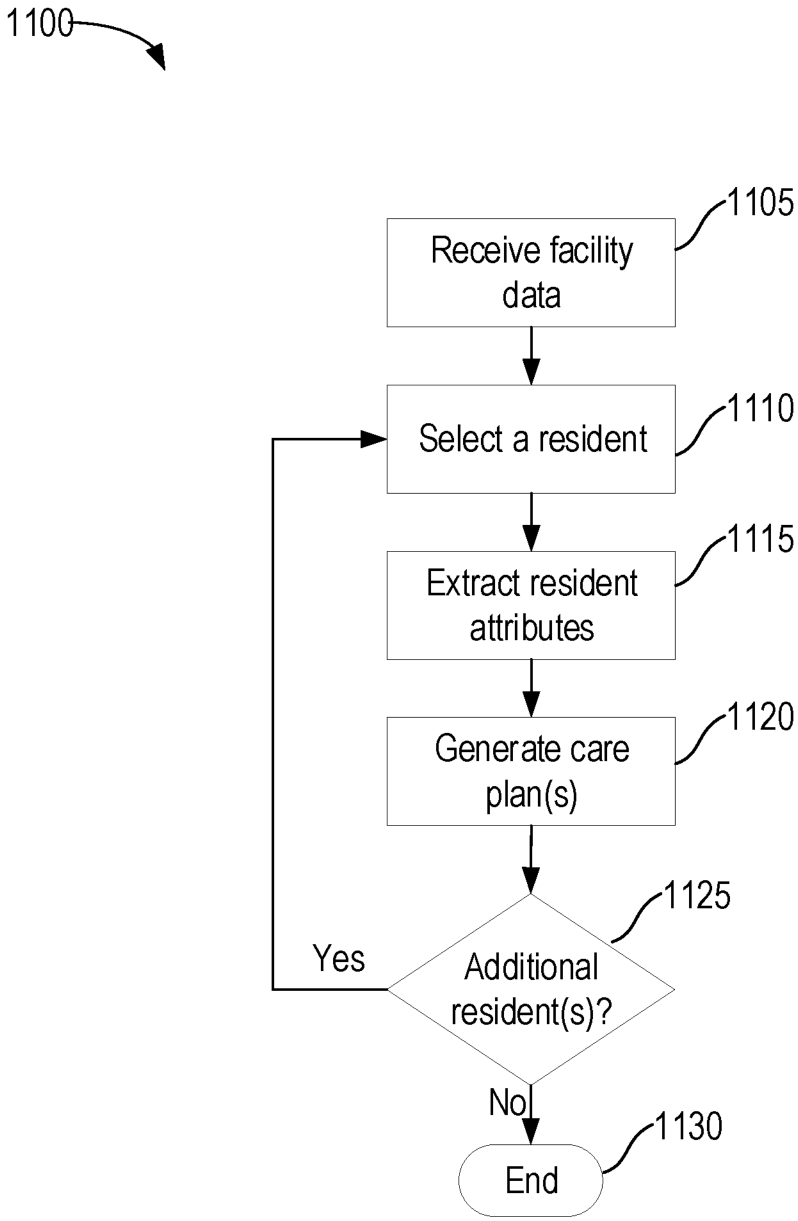
FIG. 11 is a flow diagram depicting an example method for using machine learning to generate care plans for a residential facility.

Example Method for Using Machine Learning to Generate Plans for a Residential Facility FIG. 11 is a flow diagram depicting an example method 1100 for using machine learning to generate care plans for a residential facility. In the illustrated embodiment, the method 1100 is performed by a machine learning system, such as the machine learning system 335 of FIG. 3 and/or machine learning system 435 of FIG. 4. In other embodiments, the method 1100 can be performed by other systems, such as dedicated inferencing systems.

At block 1105, the machine learning system receives facility data. In an embodiment, the facility data can generally include data relating to the residents of a given residential care facility. For example, in at least one aspect, the facility data can include, for each resident in the facility, a corresponding resident profile (e.g., including the user data 305 in FIG. 3, or reflected by the resident profile 505 of FIG. 5). As discussed above, this data can generally reflect attributes or characteristics of the residents, such as their conditions, diagnoses, assessments, medications, and the like.

In at least one embodiment, the facility data only includes information for residents that have new or changed attributes (which may therefore require a new care plan). In other embodiments, the facility data may correspond to all residents, and the machine learning system may identify those with new data (where new care plans may be needed).

At block 1110, the machine learning system selects one of the residents reflected in the facility data. Generally, this selection can be performed using any technique (including randomly or pseudo-randomly), as the machine learning system will evaluate all of the facility's residents during the method 1100. Although an iterative or sequential process is depicted for conceptual clarity, in some embodiments, the machine learning system may evaluate some or all of the user data in parallel.

At block 1115, the resident extracts relevant attributes for the selected resident. As discussed above, in some embodiments, this may generally include extracting the attributes specified for use in the machine learning model (such as fall risk, depression risk, acuity score, demographic data, and the like). In some embodiments, the resident can further extract any current conditions or problems indicated for the selected resident.

At block 1120, the machine learning system generates a set of one or more care plans for the selected resident based on the extracted conditions. For example, using the workflow 300 of FIG. 3, the method 900 of FIG. 9, and/or the method 1000 of FIG. 10, the machine learning system may process the attributes of the selected resident using the trained machine learning model(s). In at least one embodiment, as discussed above with reference to FIG. 10, the resident generates the care plans by, for each condition, evaluating a set of alternative care plan options to identify which is optimal for the current resident (e.g., based on generated recovery scores).

At block 1125, the machine learning system determines whether there is at least one additional resident in the facility that has not-yet been evaluated to generate renewed care plans. In some embodiments, this can include determining whether there are any residents with an out-of-date care plan. That is, the machine learning system can determine whether any of the remaining residents have updated data or attributes that have not been used to generate new recovery scores (and thereby generate or select new care plans), as discussed above. If so, the method 1100 can return to block 1110. If updated recovery scores and care plans have been generated for all of the residents in the facility, the method 1100 terminates at block 1130.

In embodiments, the method 1100 can be used to generate new care plans for entire facilities. In some aspects, the machine learning system may output the care plans on a GUI, enabling users to quickly review the revised care plans for the entire facility, including how they are distributed across the facility, across caregivers, and the like. For example, the machine learning system may indicate which caregivers will be using new plans, which residents or portions of the facility have a large number of new plans, and the like. Based on this information, the user (or machine learning system) may take a variety of actions, including reallocating resources (e.g., allocating increased resources and/or staff to areas where the new care plans will involve extra work).

Example Method for Refining Machine Learning Models

Figure 12:
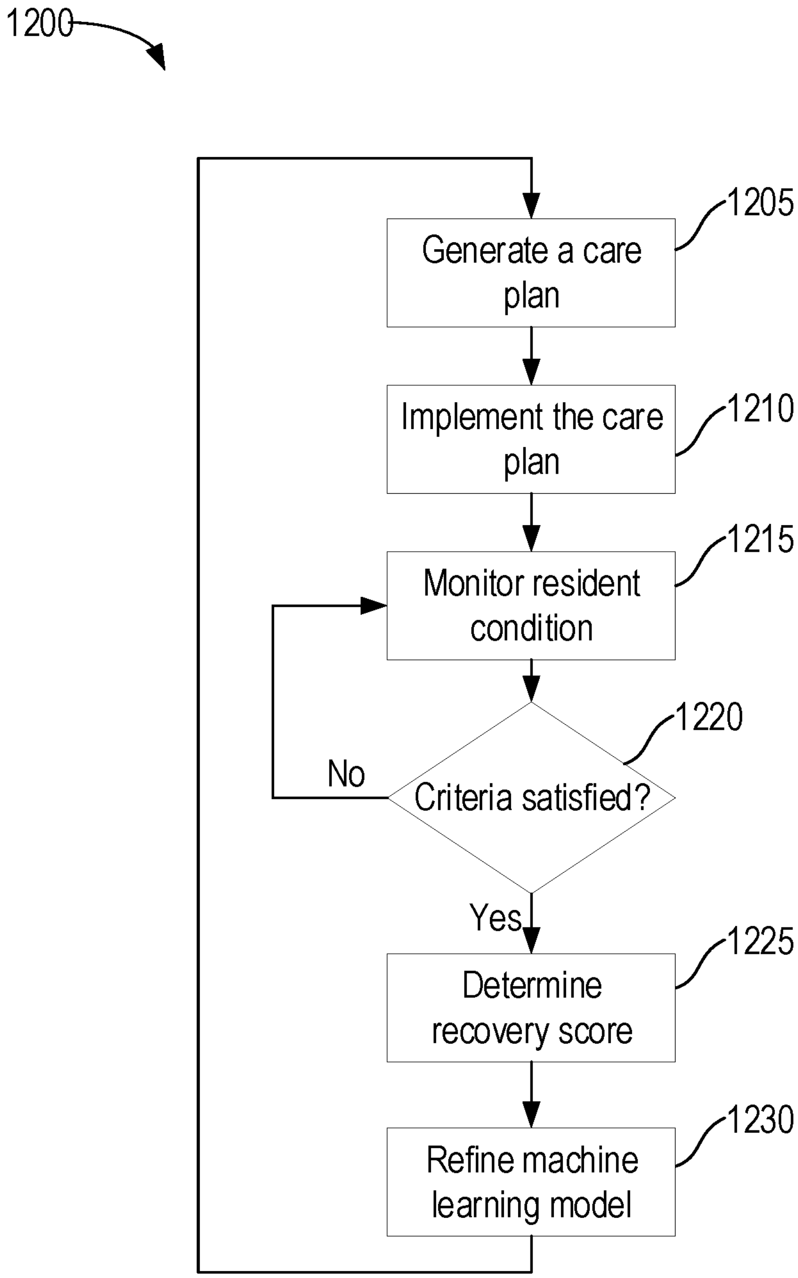
FIG. 12 is a flow diagram depicting an example method for refining machine learning models to generate and evaluate care plans.

FIG. 12 is a flow diagram depicting an example method 1200 for refining machine learning models to generate and evaluate care plans. In the illustrated embodiment, the method 1200 is performed by a machine learning system, such as the machine learning system 435 of FIG. 4. In other embodiments, the method 1200 can be performed by other systems, such as dedicated training or refinement systems.

At block 1205, the machine learning system can generate one or more care plans for a resident during runtime. That is, the machine learning system may deploy and use a trained machine learning model to process resident data in order to generate recovery scores for one or more care plans at runtime, and select one or more of these care plans for use. For example, the machine learning system may automatically use the model(s) to generate recovery scores for all possible care plans for all residents in a residential care facility, for all patients served by a clinician, and the like. Similarly, the machine learning system may automatically generate new scores whenever new data becomes available. In some embodiments, a clinician can selectively use the machine learning system to generate recovery scores and care plans as needed.

At block 1210, the machine learning system implements the care plan. In some embodiments, implementing the care plan can include outputting it to a user (e.g., a clinician) for review and approval. Once the care plan is in place, the resident begins receiving care and assistance according to the plan.

At block 1215, the machine learning system (or another system, such as the monitoring system 450 of FIG. 4)

monitors the resident condition(s) to determine whether any changes occur (such as an improvement in the condition, a worsening of the condition, complete remediation of the condition, and the like).

At block 1220, the machine learning system determines whether one or more defined criteria are satisfied. In some embodiments, the criteria can include an indication that the resident condition as changed (such as determined based on the monitoring of block 1215 above). In some embodiments, the criteria may include explicit feedback from a clinician (e.g., indicating that the care plan is inadequate or inappropriate, indicating that the resident is no longer following the care plan for other reasons, and the like).

In at least one embodiment, the criteria can include determining whether a defined period of time has elapsed. In one such embodiment, the machine learning system can determine the duration and/or target date(s) specified in the care plan (e.g., the date associated with each goal). In such an embodiment, the criteria may include determining whether the current date is equal to or later than one or more target date(s), or whether the indicated duration has elapsed. For example, one goal may indicate a target date of March 15, while another indicates a target duration of 30 days from initiation of the care plan.

If, at block 1220, the machine learning system determines that none of the criteria have passed, the method 1200 returns to block 1215. If at least one of the criteria is satisfied, the method 1200 continues to block 1225, where the machine learning system determines a recovery score for the care plan based on the resident's current condition. In one embodiment, the machine learning system determines the recovery score by evaluating the resident attributes to determine whether the condition improved, worsened, or ceased. Generally, determining that the condition has terminated will result in a higher recovery score as compared to a determination that the condition has improved but not-yet ended. Similarly, a determination that the condition improved is scored higher than a determination that the condition is unchanged, which is in turn scored higher than a determination that the condition has worsened.

In some embodiments, the recovery score is also determined at least in part on the magnitude of the change (e.g., whether the patient is 20% improved or 50% improved), where larger improvements are associated with higher scores (and larger declines are associated with smaller scores). In at least one embodiment, the recovery score is determined based in part on the length of time that has elapsed since the care plan was begun (e.g., where shorter times may be directly related to higher scores). In some embodiments, the recovery score is based on the length of time that has elapsed, as compared to the target date(s) of the care plan. For example, a care plan may receive a high recovery score if the condition was completely ameliorated, even if it took one year, if the plan was projected to take a year or more (as indicated by the target date).

In some embodiments, the machine learning system can determine this recovery score on a granular basis depending on the particular criteria that was satisfied in block 1220. For example, if the criteria was improvement of a condition, the machine learning system may generate a recovery score for all care plans, goals, and/or approaches related to that condition. If the criteria was the passing of a target date for a single goal, the machine learning system may generate a recovery score for the specific goal and/or approaches associated with that goal (as opposed to scoring the entire care plan, which may still have ongoing elements).

Once the recovery score for the relevant care plan (or portions thereof) has been generated, the method 1200 continues to block 1230. At block 1230, the machine learning system refines the trained machine learning model(s) based on this updated recovery score. For example, if the generated recovery score for a resident was relatively low, but the new data indicates that the resident has significantly improved, the machine learning system may use the prior set of attributes (used to generate the original score) as exemplar input that should be correlated with a high recovery score. Similarly, if the generated recovery score was relatively high but the new data indicates the resident condition has significantly worsened, the machine learning system may refine the model to indicate that such attributes should be correlated to a lower recovery score.

The method 1200 then returns to block 1205. In this way, the machine learning system can continuously or periodically refine the machine learning model(s), thereby ensuring that they continue to produce highly-accurate risk score predictions for residents.

Example Method for Training Machine Learning Models to Evaluate Care Plans

Figure 13:
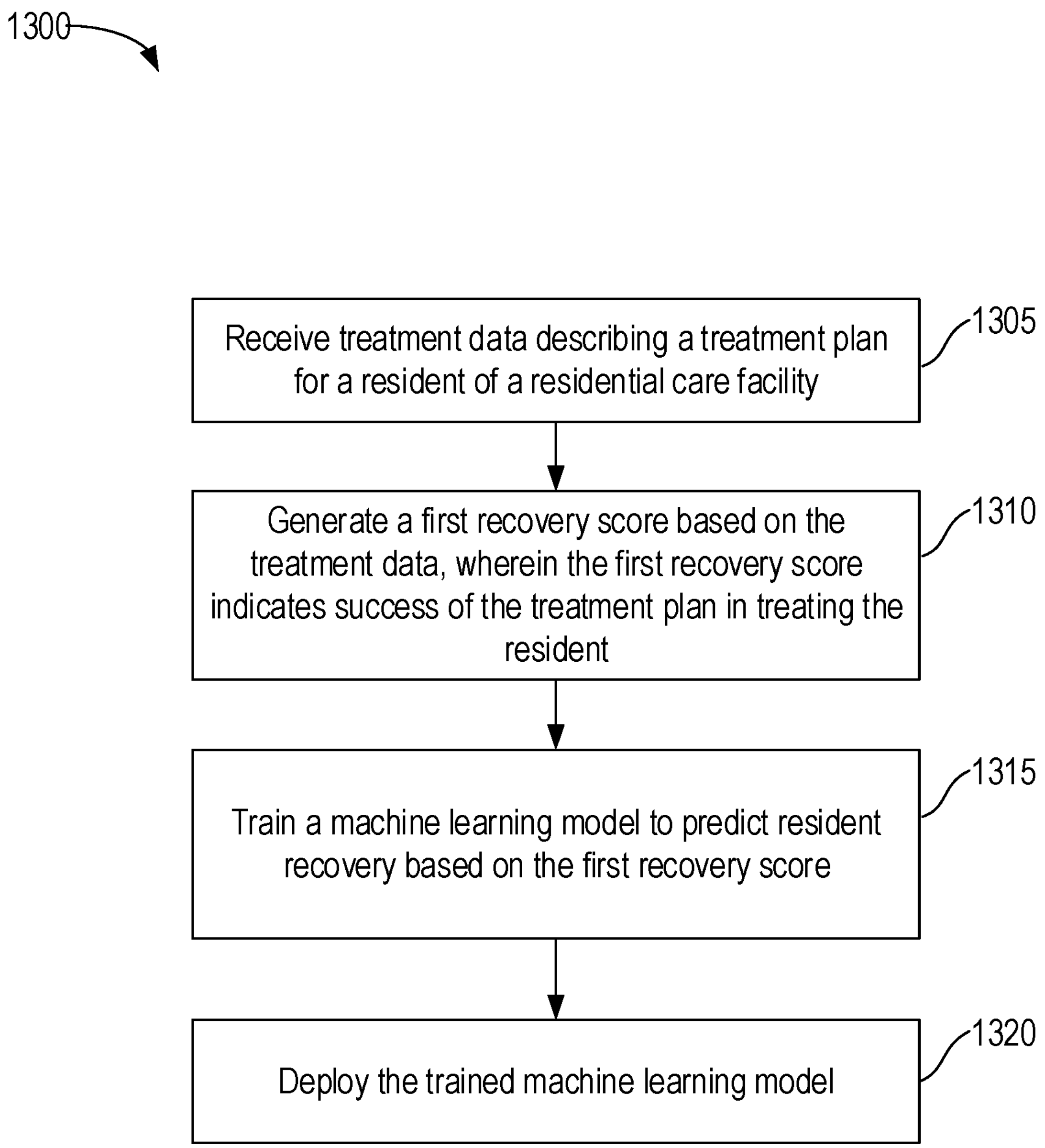
FIG. 13 is a flow diagram depicting an example method for training machine learning models to improve care planning.

FIG. 13 is a flow diagram depicting an example method for training machine learning models to improve care planning. In the illustrated embodiment, the method 1300 is performed by a machine learning system, such as the machine learning system 135 of FIG. 1. In other embodiments, the method 1300 can be performed by other systems, such as dedicated training systems.

At block 1305, treatment data (e.g., historical data 105 of FIG. 1) describing a treatment plan for a resident of a residential care facility is received.

At block 1310, a first recovery score (e.g., recovery score 245 of FIG. 2) is generated based on the treatment data, wherein the first recovery score indicates success of the treatment plan in treating the resident.

At block 1315, a machine learning model (e.g., machine learning model 140 of FIG. 1) is trained to predict resident recovery based on the first recovery score.

At block 1320, the trained machine learning model is deployed (e.g., to one or more inferencing systems).

Example Method for Generating Care Plans Using Machine Learning

Figure 14:
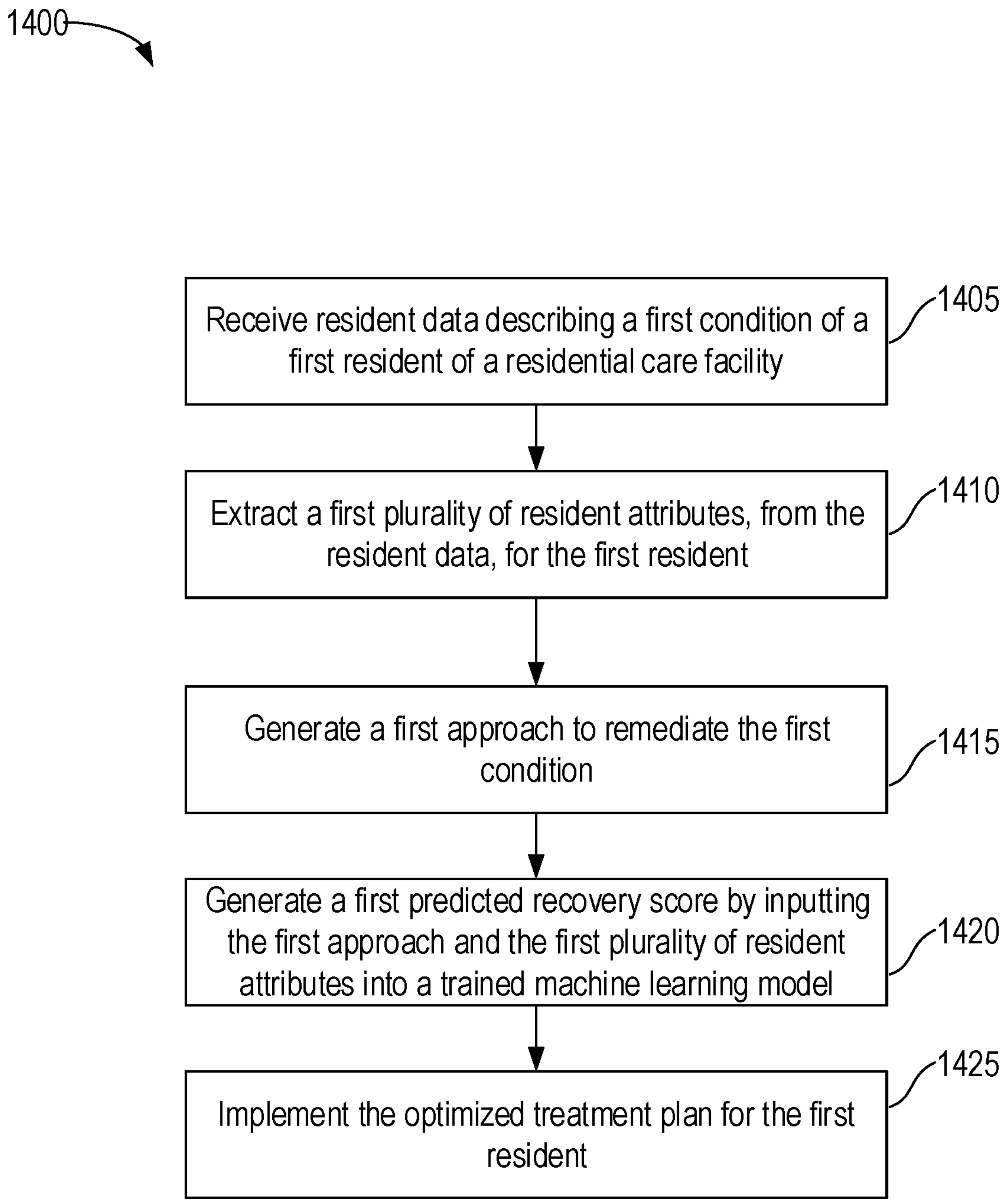
FIG. 14 is a flow diagram depicting an example method for generating and evaluating care plans using trained machine learning models.

FIG. 14 is a flow diagram depicting an example method for generating and evaluating care plans using trained machine learning models. In the illustrated embodiment, the method 1400 is performed by a machine learning system, such as the machine learning system 235 of FIG. 2. In other embodiments, the method 1400 can be performed by other systems, such as dedicated inferencing systems.

At block 1405, resident data (e.g., resident data 305 of FIG. 3) describing a first condition of a first resident of a residential care facility is received.

At block 1410, a first plurality of resident attributes (e.g., resident attributes 310 of FIG. 3) is extracted for the first resident from the resident data.

At block 1415, a first approach to remediate the first condition is generated.

At block 1420, a first predicted recovery score (e.g., recovery score 345 of FIG. 3) is generated by inputting the first approach and the first plurality of resident attributes into a trained machine learning model.

At block 1425, the optimized treatment plan (e.g., care plan 340 of FIG. 3) is implemented for the first resident.

Example Processing System for Improved Machine Learning

Figure 15:
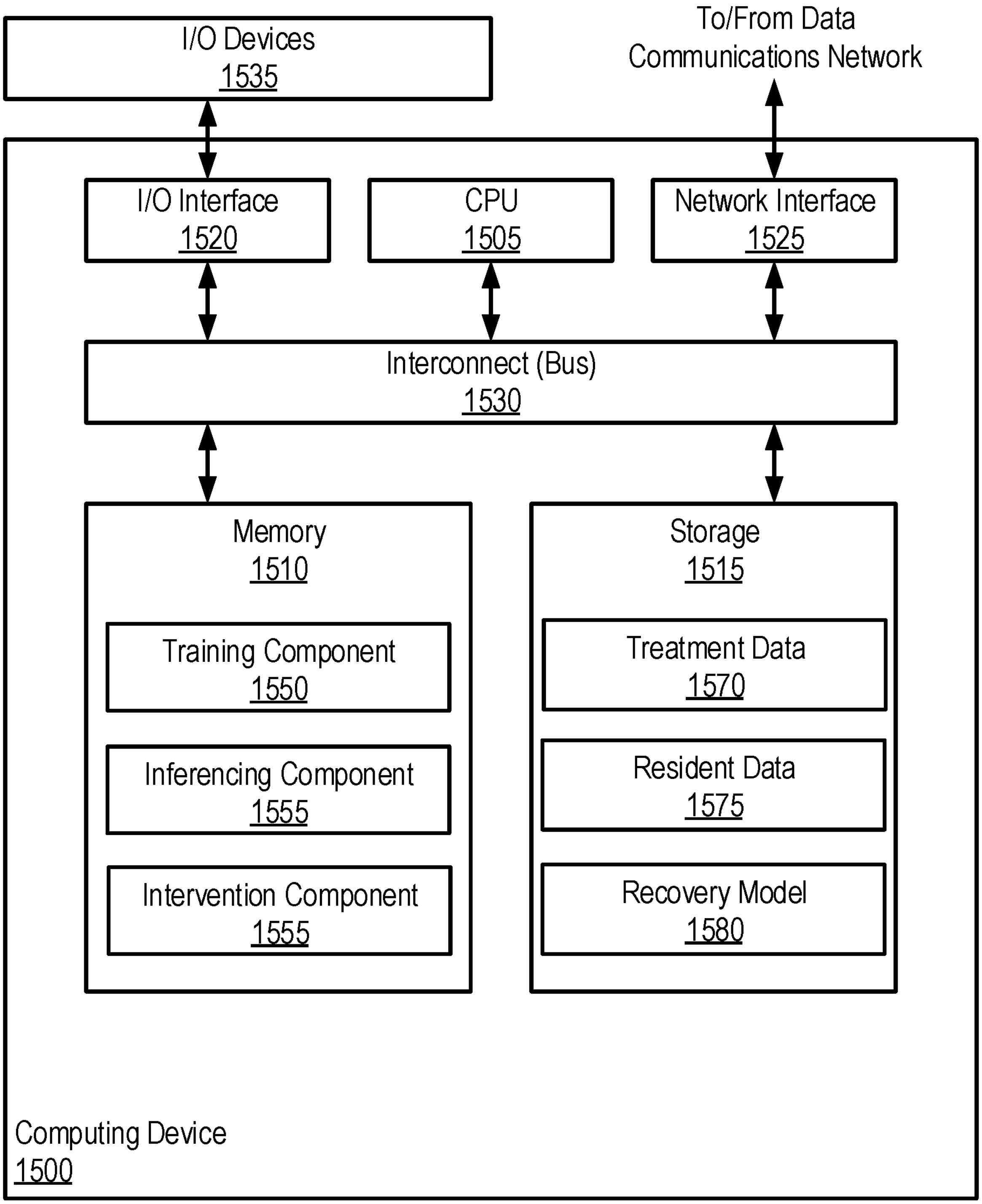
FIG. 15 depicts an example computing device configured to perform various aspects of the present disclosure.

FIG. 15 depicts an example computing device 1500 configured to perform various aspects of the present disclosure. Although depicted as a physical device, in embodiments, the computing device 1500 may be implemented using virtual device(s), and/or across a number of devices (e.g., in a cloud environment). In one embodiment, the computing device 1500 corresponds to the machine learning system 135 of FIG. 1, the machine learning system 235 of FIG. 2, the machine learning system 335 of FIG. 3, and/or the machine learning system 435 of FIG. 4.

As illustrated, the computing device 1500 includes a CPU 1505, memory 1510, storage 1515, a network interface 1525, and one or more I/O interfaces 1520. In the illustrated embodiment, the CPU 1505 retrieves and executes programming instructions stored in memory 1510, as well as stores and retrieves application data residing in storage 1515. The CPU 1505 is generally representative of a single CPU and/or GPU, multiple CPUs and/or GPUs, a single CPU and/or GPU having multiple processing cores, and the like. The memory 1510 is generally included to be representative of a random access memory. Storage 1515 may be any combination of disk drives, flash-based storage devices, and the like, and may include fixed and/or removable storage devices, such as fixed disk drives, removable memory cards, caches, optical storage, network attached storage (NAS), or storage area networks (SAN).

In some embodiments, I/O devices 1535 (such as keyboards, monitors, etc.) are connected via the I/O interface(s) 1520. Further, via the network interface 1525, the computing device 1500 can be communicatively coupled with one or more other devices and components (e.g., via a network, which may include the Internet, local network(s), and the like). As illustrated, the CPU 1505, memory 1510, storage 1515, network interface(s) 1525, and I/O interface(s) 1520 are communicatively coupled by one or more buses 1530.

In the illustrated embodiment, the memory 1510 includes a training component 1550, an inferencing component 1555, and an intervention component 1560, which may perform one or more embodiments discussed above. Although depicted as discrete components for conceptual clarity, in embodiments, the operations of the depicted components (and others not illustrated) may be combined or distributed across any number of components. Further, although depicted as software residing in memory 1510, in embodiments, the operations of the depicted components (and others not illustrated) may be implemented using hardware, software, or a combination of hardware and software.

In one embodiment, the training component 1550 is used to generate training data and/or to train machine learning models (e.g., based on historical training data), as discussed above. The inferencing component 1555 may generally be used to generate recovery scores and/or generate or select care plans for residents, as discussed above. The intervention component 1560 may be configured to use the generated recovery scores to select, generate, and/or implement various care plans, as discussed above.

In the illustrated example, the storage 1515 includes treatment data 1570 (which may correspond to historical data, such as historical data 105 of FIG. 1 and/or historical data 205 of FIG. 2), as well as resident data 1575 (which may correspond to resident data 305 of FIG. 3, and/or resident data 405 of FIG. 4). The storage 1515 also includes a recovery model 1580 (which may correspond to the machine learning model 140 of FIG. 1). Although depicted as residing in storage 1515, the treatment data 1570, resident data 1572, and recovery model 1580 may be stored in any suitable location, including memory 1510.

Example Clauses

Implementation examples are described in the following numbered clauses:

Clause 1: A method, comprising: receiving treatment data describing a treatment plan for a resident of a residential care facility; generating a first recovery score based on the treatment data, wherein the first recovery score indicates success of the treatment plan in treating the resident; training a machine learning model to predict resident recovery based on the first recovery score; and deploying the trained machine learning model.

Clause 2: The method of Clause 1, wherein the treatment plan comprises: a condition of the resident, a goal for remediation of the condition, and an approach to achieve the goal.

Clause 3: The method of any one of Clauses 1-2, wherein generating the first recovery score comprises: determining, based on the treatment data, whether the goal was reached, based on determining whether the approach successfully remediated the condition; in response to determining that the goal was reached, determining, based on the treatment data, an amount of time that elapsed before the goal was reached; and computing the first recovery score based at least in part on the amount of time.

Clause 4: The method of any one of Clauses 1-3, further comprising: extracting, from the treatment data, a plurality of resident attributes describing the resident; and training the machine learning model based further on the plurality of resident attributes.

Clause 5: The method of any one of Clauses 1-4, wherein training the machine learning model comprises: generating a predicted recovery score by processing the treatment plan and the plurality of resident attributes using the machine learning model; and refining the machine learning model based on a difference between the predicted recovery score and the first recovery score.

Clause 6: A method, comprising: receiving resident data describing a first condition of a first resident of a residential care facility; selecting an optimized treatment plan for the first resident, comprising: extracting a first plurality of resident attributes, from the resident data, for the first resident; generating a first approach to remediate the first condition; and generating a first predicted recovery score by inputting the first approach and the first plurality of resident attributes into a trained machine learning model; and implementing the optimized treatment plan for the first resident.

Clause 7: The method of Clause 6, wherein implementing the optimized treatment plan comprises: outputting the first approach to a clinician; and receiving approval, from the clinician, of the first approach.

Clause 8: The method of any one of Clauses 6-7, wherein outputting the first approach comprises displaying the first approach and the first predicted recovery score on a graphical user interface (GUI).

Clause 9: The method of any one of Clauses 6-8, wherein selecting the optimized treatment plan comprises: generating a plurality of predicted recovery scores by processing a plurality of alternate approaches using the trained machine learning model; and selecting the first approach based on determining that the first predicted recovery score is greater than each of the plurality of predicted recovery scores.

Clause 10: The method of any one of Clauses 6-9, wherein the first approach comprises one or more medical interventions to remediate the first condition.

Clause 11: The method of any one of Clauses 6-10, further comprising: determining whether the first approach succeeded in remediating the first condition; and refining the trained machine learning model based on whether the first approach succeeded in remediating the first condition.

Clause 12: The method of any one of Clauses 6-13, further comprising, upon determining that at least one of the first plurality of resident attributes changed after the optimized treatment plan was implemented: extracting a new plurality of resident attributes for the first resident; generating a new approach to remediate the first condition; and generating a new predicted recovery score by processing the new approach and the new plurality of resident attributes using the trained machine learning model.

Clause 13: The method of any one of Clauses 6-12, further comprising, for each respective resident of a plurality of residents in the residential care facility: selecting a respective optimized treatment plan for the respective resident, comprising: extracting a respective plurality of resident attributes for the respective resident; generating a respective approach to remediate the respective condition; and generating a respective predicted recovery score by processing the respective approach and the respective plurality of resident attributes using the trained machine learning model; and implementing the respective optimized treatment plan for the respective resident.

Clause 20: A system, comprising: a memory comprising computer-executable instructions; and one or more processors configured to execute the computer-executable instructions and cause the processing system to perform a method in accordance with any one of Clauses 1-13.

Clause 21: A system, comprising means for performing a method in accordance with any one of Clauses 1-13.

Clause 22: A non-transitory computer-readable medium comprising computer-executable instructions that, when executed by one or more processors of a processing system, cause the processing system to perform a method in accordance with any one of Clauses 1-13.

Clause 23: A computer program product embodied on a computer-readable storage medium comprising code for performing a method in accordance with any one of Clauses 1-13.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or systems (e.g., the machine learning system 135) or related data available in the cloud. For example, the machine learning system 135 could execute on a computing system in the cloud and train and/or use machine learning models. In such a case, the machine learning system 135 could train models to generate depression risk scores, and store the models at a storage location in the cloud. Doing so allows a user to access this information from any computing system attached to a network connected to the cloud (e.g., the Internet).

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method, comprising:

receiving treatment data describing a historical treatment plan for a historical resident of a residential care facility;

generating a historical recovery score based on the treatment data, wherein the historical recovery score indicates success of the historical treatment plan in treating the historical resident, wherein the historical recovery score is inversely related to an amount of time that elapsed while the historical resident used the historical treatment plan;

training one or more machine learning models based on the historical recovery score;

deploying the trained one or more machine learning models;

receiving resident data describing a first condition of a first resident of the residential care facility, wherein the resident data comprises only updated data that has changed since a last time a treatment plan was generated for the first resident;

in response to determining, at a first point in time, that a current time is not within a specified off-peak time, refraining from processing the resident data at the first point in time;

in response to determining, at a second point in time subsequent to the first point in time, that the current time is within a specified off-peak time when additional computational resources are available as compared to a specified peak time, automatically selecting, by a computing system, a first treatment plan for the first resident using the trained one or more machine learning models, comprising:

extracting a first plurality of resident attributes from the resident data for the first resident;

determining a first goal for a first condition of the first resident;

generating a first achievability score based on processing the first goal and the first plurality of resident attributes using a first machine learning model;

generating a first approach to achieve the first goal;

generating a first efficacy score by processing the first goal, the first approach, and the first plurality of resident attributes using a second machine learning model, wherein the first efficacy score indicates an amount of time that is predicted to elap se prior to achieving the first goal;

generating a first predicted recovery score based on the first achievability score and the first efficacy score;

generating a second predicted recovery score for a second treatment plan; and determining that the first predicted recovery score is greater than the second predicted recovery score;

storing, by the computing system, the second treatment plan and the second predicted recovery score;

automatically implementing, bythe computing system, the first treatment plan for the first resident, wherein the first treatment plan comprises the first approach, comprising allocating increased resources to an area where the first treatment plan will be provided to the first resident; and subsequent to implementing the first treatment plan, implementing the stored second treatment plan without additional execution of the second machine learning model.

2. The method of claim 1, wherein the historical treatment plan comprises:

a condition of the historical resident, a goal for remediation of the condition, and an approach to achieve the goal.

3. The method of claim 2, wherein generating the historical recovery score comprises:

determining, based on the treatment data, whether the goal was reached, based on determining whether the approach successfully remediated the condition; and in response to determining that the goal was reached, determining, the amount of time based on determining a time that elapsed before the goal was reached.

4. The method of claim 1, further comprising:

extracting, from the treatment data, a plurality of historical resident attributes describing the historical resident; and training the one or more machine learning models based further on the plurality of historical resident attributes.

5. The method of claim 4, wherein training the one or more machine learning model comprises:

generating a predicted historical recovery score by processing the historical treatment plan and the plurality of historical resident attributes using the second machine learning model; and refining the second machine learning model based on a difference between the predicted historical recovery score and the historical recovery score.

6. A method, comprising:

receiving resident data describing a first condition of a first resident of a residential care facility, wherein the resident data comprises only updated data that has changed since a last time a treatment plan was generated for the first resident;

in response to determining, at a first point in time, that a current time is not within a specified off- peak time, refraining from processing the resident data at the first point in time;

in response to determining, at a second point in time subsequent to the first point in time, that the current time is within a specified off-peak time when additional computational resources are available as compared to a specified peak time, automatically selecting, by a computing system, a first treatment plan for the first resident, comprising:

extracting a first plurality of resident attributes, from the resident data, for the first resident;

determining a first goal for the first condition;

generating a first achievability score based on processing the first goaland the first plurality of resident attributes using a first machine learning model;

generating a first approach to achieve the first goal;

generating a first efficacy score by processing the first goal, the first approach, and the first plurality of resident attributes using a second machine learning model, wherein the first efficacy score indicates an amount of time that is predicted to elap se prior to achieving the first goal;

generating a first predicted recovery score based on the first achievability score and the first efficacy score;

generating a second predicted recovery score for a second treatment plan; and determining that the first predicted recovery score is greater than the second predicted recovery score;

storing, by the computing system, the second treatment plan and the second predicted recovery score;

automatically implementing, bythe computing system, the first treatment plan for the first resident, wherein the first treatment plan comprises the first approach, comprising allocating increased resources to an area where the first treatment plan will be provided to the first resident; and subsequent to implementing the first treatment plan, implementing the stored second treatment plan without additional execution of the second machine learning model.

7. The method of claim 6, wherein implementing the first treatment plan comprises:

outputting the first approach to a clinician; and receiving approval, from the clinician, of the first approach.

8. The method of claim 7, wherein outputting the first approach comprises displaying the first approach and the first predicted recovery score on a graphical user interface.

9. The method of claim6, wherein selecting the first treatment plan comprises:

generating a plurality of predicted recovery scores by processing a plurality of alternate approaches using the second machine learning model; and selecting the first approach based on determining that the first predicted recovery score is greater than each of the plurality of predicted recovery scores.

10. The method of claim 6, wherein the first approach comprises one or more medical interventions to remediate the first condition.

11. The method of claim 6, further comprising:

determining whether the first approach succeeded in remediating the first condition; and refining the second machine learning model based on whether the first approach succeeded in remediating the first condition.

12. The method of claim 6, further comprising, upon determining that at least one of the first plurality of resident attributes changed after the first treatment plan was implemented:

extracting a new plurality of resident attributes for the first resident;

generating a new approach to remediate the first condition; and generating a new predicted recovery score by processing the new approach and the new plurality of resident attributes using the second machine learning model.

13. The method of claim 6, further comprising, for each respective resident of a plurality of residents in the residential care facility:

selecting a respective treatment plan for the respective resident, comprising:

extracting a respective plurality of resident attributes for the respective resident;

generating a respective approach to remediate the respective condition; and generating a respective predicted recovery score by processing the respective approach and the respective plurality of resident attributes using the second machine learning model; and implementing the respective treatment plan for the respective resident.

14. A non-transitory computer-readable storage medium comprising computer-readable program code that, when executed using one or more computer processors, performs an operation comprising:

receiving resident data describing a first condition of a first resident of a residential care facility, wherein the resident data comprises only updated data that has changed since a last time a treatment plan was generated for the first resident;

in response to determining, at a first point in time, that a current time is not within a specified off- peak time, refraining from processing the resident data at the first point in time;

in response to determining, at a second point in time subsequent to the first point in time, that the current time is within a specified off-peak time when additional computational resources are available as compared to a specified peak time, automatically selecting, by a computing system, a first treatment plan for the first resident, comprising:

extracting a first plurality of resident attributes, from the resident data, for the first resident;

determining a first goal for the first condition;

generating a first achievability score based on processing the first goaland the first plurality of resident attributes using a first machine learning model;

generating a first approach to achieve the first goal;

generating a first efficacy score by processing the first goal, the first approach, and the first plurality of resident attributes using a second machine learning model, wherein the first efficacy score indicates an amount of time that is predicted to elapse prior to achieving the first goal; and generating a first predicted recovery score based on the first achievability score and the first efficacy score;

generating a second predicted recovery score for a second treatment plan; and determining that the first predicted recovery score is greater than the second predicted recovery score;

storing, by the computing system, the second treatment plan and the second predicted recovery score;

automatically implementing, bythe computing system, the first treatment plan forthe first resident, wherein the first treatment plan comprises the first approach, comprising allocating increased resources to an area where the first treatment plan will be provided to the first resident; and subsequent to implementing the first treatment plan, implementing the stored second treatment plan without additional execution of the second machine learning model.

15. The non-transitory computer-readable storage medium of claim 14, wherein implementing the first treatment plan comprises:

outputting the first approach to a clinician; and receiving approval, from the clinician, of the first approach.

16. The non-transitory computer-readable storage medium of claim 14, wherein selecting the first treatment plan comprises:

generating a plurality of predicted recovery scores byprocessing a plurality of alternate approaches using the second machine learning model; and selecting the first approach based on determining that the first predicted recovery score is greater than each of the plurality of predicted recovery scores.

17. The non-transitory computer-readable storage medium of claim 14, wherein the first approach comprises one or more medical interventions to remediate the first condition.

18. The non-transitory computer-readable storage medium of claim 14, the operation further comprising:

determining whether the first approach succeeded in remediating the first condition; and refining the second machine learning model based on whether the first approach succeeded in remediating the first condition.

19. The non-transitory computer-readable storage medium of claim 14, the operation further comprising, upon determining that at least one of the first plurality of resident attributes changed after the first treatment plan was implemented:

extracting a new plurality of resident attributes for the first resident;

generating a new approach to remediate the first condition; and generating a new predicted recovery score by processing the new approach and the new plurality of resident attributes using the second machine learning model.

20. The non-transitory computer-readable storage medium of claim 14, the operation further comprising, for each respective resident of a plurality of residents in the residential care facility:

selecting a respective treatment plan for the respective resident, comprising:

extracting a respective plurality of resident attributes for the respective resident;

generating a respective approach to remediate the respective condition; and generating a respective predicted recovery score by processing the respective approach and the respective plurality of resident attributes using the second machine learning model; and implementing the respective treatment plan for the respective resident.

* * * * *